United States Patent
Jankowski et al.

(10) Patent No.: US 11,839,644 B2
(45) Date of Patent: *Dec. 12, 2023

(54) COMPOSITIONS AND METHODS FOR TREATMENT OF CUTANEOUS OR MUSCLE INCISION PAIN

(71) Applicant: Children's Hospital Medical Center, Cincinnati, OH (US)

(72) Inventors: Michael P. Jankowski, Union, KY (US); Xiaohua Liu, Cincinnati, OH (US); John Barns Rose, Cincinnati, OH (US)

(73) Assignee: CHILDREN'S HOSPITAL MEDICAL CENTER, Cincinnati, OH (US)

( * ) Notice: Subject to any disclaimer, the term of this patent is extended or adjusted under 35 U.S.C. 154(b) by 499 days.

This patent is subject to a terminal disclaimer.

(21) Appl. No.: 16/985,274

(22) Filed: Aug. 5, 2020

(65) Prior Publication Data

US 2020/0376086 A1 Dec. 3, 2020

Related U.S. Application Data

(63) Continuation of application No. 16/180,085, filed on Nov. 5, 2018, now Pat. No. 10,765,725, which is a continuation of application No. 15/349,651, filed on Nov. 11, 2016, now Pat. No. 10,155,026.

(60) Provisional application No. 62/262,594, filed on Dec. 3, 2015.

(51) Int. Cl.
*A61K 38/27* (2006.01)

(52) U.S. Cl.
CPC .................................... *A61K 38/27* (2013.01)

(58) Field of Classification Search
CPC ..................................................... A61K 38/27
See application file for complete search history.

(56) References Cited

U.S. PATENT DOCUMENTS

| | | |
|---|---|---|
| 5,378,686 A | 1/1995 | Bennett |
| 5,965,520 A | 10/1999 | Bennett |
| 10,155,026 B2 | 12/2018 | Jankowski et al. |
| 10,765,725 B2 | 9/2020 | Jankowski et al. |

OTHER PUBLICATIONS

Beland, B, et al., "Influence of Peripheral Inflammation on the Postnatal Maturation of Primary Sensory Neuron Phenotype in Rats," J Pain 2001, 2(1):36-45, 10 pgs.
Bennett, MD, R., "Growth Hormone in Musculoskeletal Pain States," Current Pain and Headache Reports, 2005, 9:331-338, 8 pgs.
Bennett, RM., "Disordered growth hormone secretion in fibromyalgia: a review of recent findings and a hypothesized etiology," Z Rheumatol., 1998, 57(Suppl 2):72-6, 5 pgs.
Bjersing, JL, et al., "Changes in pain and insulin-like growth factor 1 in fibromyalgia during exercise: the involvement of cerebrospinal inflammatory factors and neuropeptides," Arthritis Res. Ther., 2012, 14:R162, 9 pgs.
Choi, Y-S, et al., "IGF-1 Receptor-Mediated ERK/MAPK Signaling Couples Status Epilepticus to Progenitor Cell Proliferation in the Subgranular Layer of the Dentate Gyrus," GLIA, 2008, 56:791-800, 10 pgs.
Chong, PKK, et al., "Energy expenditure and body composition in growth hormone deficient adults on exogenous growth hormone," Clin. Endocrinol., 1994, 40:103-110, 8 pgs.
Cimaz, R., et al., "Unexpected healing of cutaneous ulcers in a short child," Lancet, Jul. 21, 2001, 358:211-2, 2 pgs.
Craner, MJ, et al., "Preferential expression of IGF-I in small DRG neurons and down-regulation following injury," NeuroReport, 2002, 13(13):1649-52, 4 pgs.
Cuatrecasas, G., et al., "GH/IGF1 axis disturbances in the fibromyalgia syndrome: is there a rationale for GH treatment?" Pituitary, 2014, 17:277-83, 7 pgs.
Cuatrecasas, G., et al., "High Prevalence of Growth Hormone Deficiency in Severe Fibromyalgia Syndromes," J Clin Endocrin Metab, 2010, 95(9):4331-37, 7 pgs.
Cuatrecasas, G.., et al., "Growth hormone treatment for sustained pain reduction and improvement in quality of life in severe fibromyalgia," Pain, 2012, 153:1382-89, 8 pgs.
De Lima, J., et al., "Sensory hyperinnervation after neonatal skin wounding: effect of bupivacaine sciatic nerve block," Br J Anaesth, 1999, 83(4):662-4, 3 pgs.
Elitt, C.M., et al., "Artemin Overexpression in Skin Enhances Expression of TRPV1 and TRPA1 in Cutaneous Sensory Neurons and Leads to Behavioral Sensitivity to Heat and Cold," J Neurosci, 2006, 26(33):8578-87, 10 pgs.
Farris, G.M., et al., "Recombinant Rat and Mouse Growth Hormones: Risk Assessment of Carcinogenic Potential in 2-Year Bioassays in Rats and Mice," Toxicol Sci, 2007, 97(2):548-61, 14 pgs.
Fitzgerald, M., et al., "Postnatal Development of the Cutaneous Flexor Reflex: Comparative Study of Preterm Infants and Newborn Rat Pups," Developmental Medicine and Child Neurology, 1988, 30:520-26, 7 pgs.
Fitzgerald, M., et al., "The Neurobiology of Pain: Developmental Aspects," The Neuroscientist, 2001, 7(3):246-57, 12 pgs.
Garcia, J.M., et al., "Ghrelin Prevents Cisplatin-Induced Mechanical Hyperalgesia and Cachexia," Endocrinology, 2008, 149(2):455-60, 6 pgs.

(Continued)

*Primary Examiner* — Elly-Gerald Stoica
(74) *Attorney, Agent, or Firm* — Frost Brown Todd LLP

(57) ABSTRACT

Disclosed are methods of treating pain in a mammal, which may include the step of administering human growth hormone to a mammal in need thereof The pain treated by the disclosed methods may be of a type caused by inflammation induced mechanical and/or thermal hypersensitivity, and may include, for example, a pain type resulting from one or more conditions selected from peripheral injury pain, post-operative pain, cutaneous inflammation, cutaneous incision, muscle incision, or chronic pain. Disease states in which the disclosed methods may be used include fibromyalgia, sickle cell anemia, epidermolysis bullosa, erythromelalgia, complex regional pain syndrome, or generalized muscle pain.

11 Claims, 17 Drawing Sheets

Specification includes a Sequence Listing.

(56) References Cited

OTHER PUBLICATIONS

Gartner, M.H., et al., "Insulin-like Growth Factors I and II Expression in the Healing Wound," J Surg Res, 1992, 52:389-394, 6 pgs.
Gennaro, A.R., Ed., *Remington's Pharmaceutical Sciences*, 18th Ed., Mack Publ. Co., Easton, PA, 1990, 8 pgs.
Goodrich, C.A., "Measurement of body temperature in neonatal mice," J Appl Physiol, 1977, 43:1102-5, 4 pgs.
Herndon, MD, D.N., et al., "Characterization of Growth Hormone Enhanced Donor Site Healing in Patients with Large Cutaneous Burns," Ann Surg, 1995, 221(6):649-59, 8 pgs.
Jankowski, M.P., et al., "Age-dependent sensitization of cutaneous nociceptors during developmental inflammation," Mol Pain, 2014, 10:34, 18 pgs.
Jankowski, M.P., et al., "Enhanced Artemin/GFRα3 Levels Regulate Mechanically Insensitive, Heat-Sensitive C-Fiber Recruitment after Axotomy and Regeneration," J Neurosci, 2010, 30(48):16272-16283, 12 pgs.
Jankowski, M.P., et al., "Purinergic receptor P2Y1 regulates polymodal C-fiber thermal thresholds and sensory neuron phenotypic switching during peripheral inflammation," Pain, Feb. 2012, 153(2):410-419, 21 pgs.
Jankowski, M.P., et al., "Sensitization of Cutaneous Nociceptors After Nerve Transection and Regeneration: Possible Role of Target-Derived Neurotrophic Factor Signaling," J Neurosci. 2009, 29(6):1636-47, 12 pgs.
Jankowski, M.P., et al., "Sox11 transcription factor modulates peripheral nerve regeneration in adult mice," Brain Res, 2009, 1256:43-54, 18 pgs.
Jankowski, M.P., et al., "SRY-Box Containing Gene 11 (Sox11) Transcription Factor Is Required for Neuron Survival and Neurite Growth," Neuroscience, 2006, 143(2):501-514, 28 pgs.
Jennings, E., et al., "Postnatal changes in responses of rat dorsal horn cells to afferent stimulation: a fibre-induced sensitization," J Physiol, 1998, 509(Pt 3):859-68, 10 pgs.
Kastrup, Y., et al., "Distribution of Growth Hormone Receptor mRNA in the Brain and Spinal Cord of the Rat," Neuroscience, 2005, 130:419-25, 7 pgs.
Koch, S.C., et al., "C-fiber activity-dependent maturation of glycinergic inhibition in the spinal dorsal horn of the postnatal rat," PNAS, Jul. 2012, 109(30):12201-06, 6 pgs.
Koltzenburg, M., et al., "Receptive Properties of Mouse Sensory Neurons Innervating Hairy Skin," J Neurophysiol, 1997, 78:1841-1850, 10 pgs.
Kress, M., et al., "Responsiveness and Functional Attributes of Electrically Localized Terminals of Cutaneous C-Fibers In Vivo and In Vitro," J Neurophysiol, 1992, 68(2):581-595, 15 pgs.
Kurimoto, K., et al., "An improved single-cell cDNA amplification method for efficient high-density oligonucleotide microarray analysis," Nucleic Acids Res, 2006, 34(5):e42, 17 pgs.
Landis, C.A., et al., "Decreased Nocturnal Levels of Prolactin and Growth Hormone in Women with Fibromyalgia," J Clin Endocrinol Metab, 2001, 86(4):1672-8, 7 pgs.
Lanning, N.J., et al., "Recent advances in growth hormone signaling," Rev Endocr Metab Disord, 2007, 7:225-235, 11 pgs.
Lawson, J.J., et al., "TRPV1 Unlike TRPV2 Is Restricted to a Subset of Mechanically Insensitive Cutaneous Nociceptors Responding to Heat," J Pain, 2008, 9(4):298-308, 18 pgs.
Leal-Cerro, A., et al., "The Growth Hormone (GH)-Releasing Hormone-GH-Insulin-like Growth Factor-1 Axis in Patients with Fibromyalgia Syndrome," J Clin Endocrinol Metab, 1999, 84(9):3378-81, 4 pgs.
Lee, S-M, et al., "Activation and Repression of Cellular Immediate Early Genes by Serum Response Factor Cofactors," J Biol Chem, 2010, 285(29):22036-22049, 14 pgs.
Li, J., et al., "Excitatory synapses in the rat superficial dorsal horn are strengthened following peripheral inflammation during early postnatal development," Pain, 2009, 143:56-64, 9 pgs.
Li, J., et al., "Pacemaker neurons within newborn spinal pain circuits," J Neurosci, 2011, 31(24):9010-9022, 30 pgs.

Li, X., et al., "α2A-Adrenoceptor Stimulation Reduces Capsaicin-Induced Glutamate Release from Spinal Cord Synaptosomes," The Journal of Pharmacology and Experimental Therapeutics, 2001, 299(3):939-944, 6 pgs.
Light, A.R., et al., "Dorsal Root Ganglion Neurons Innervating Skeletal Muscle Respond to Physiological Combinations of Protons, ATP, and Lactate Mediated by ASIC, P2X, and TRPV1," J Neurophysiol, 2008, 100:1184-1201, 18 pgs.
Light, A.R., et al., "Gene expression alterations at baseline and following moderate exercise in patients with chronic fatigue syndrome and fibromyalgia syndrome," J Intern Med, 2012, 271(1):64-81, 28 pgs.
Luo, W., et al., "A Hierarchical NGF Signaling Cascade Controls Ret-Dependent and Ret-Independent Events during Development of Nonpeptidergic DRG Neurons," Neuron, 2007, 54:739-754, 16 pgs.
Luo, W., et al., "Molecular Identification of Rapidly Adapting Mechanoreceptors and their Developmental Dependence on Ret Signaling," Neuron, 2009, 64(6):841-56, 25 pgs.
Malemud, C.J., "The basis for medical therapy of fibromyalgia with growth hormone," Pain, 2012, 153:1342-1343, 2 pgs.
Malin, S.A., et al., "Production of dissociated sensory neuron cultures and considerations for their use in studying neuronal function and plasticity," Nat Protoc, 2007, 2(1):152-60, 10 pgs.
Marsh, D., et al., "Epidural opioid analgesia in infant rats I: mechanical and heat responses," Pain, 1999, 82:23-32, 10 pgs.
Marsh, D., et al., "Epidural opioid analgesia in infant rats II: responses to carrageenan and capsaicin," Pain, 1999, 82:33-38, 6 pgs.
Mearow, K.M., et al., "Increased NGF mRNA expression in denervated rat skin," NeuroReport, 1993, 4:351-4, 4 pgs.
Miura, M., et al., "Peripheral sensitization caused by insulin-like growth factor 1 contributes to pain hypersensitivity after tissue injury," Pain, 2011, 152:888-895, 8 pgs.
Molliver, D.C., et al., "IB4-Binding DRG Neurons Switch from NGF to GDNF Dependence in Early Postnatal Life," Neuron, 1997, 19:849-861, 13 pgs.
Molliver, D.C., et al., "The ADP receptor $P2Y_1$ is necessary for normal thermal sensitivity in cutaneous polymodal nociceptors," Mol Pain, 2011, 7:13, 12 pgs.
Nathan, MD, A., et al., "Primary Erythromelalgia in a Child Responding to Intravenous Lidocaine and Oral Mexiletine Treatment," Pediatrics, 2005, 115:e504-7, 6 pgs.
Pogatzki, E.M., et al., "Characterization of Aδ- and C-Fibers Innervating the Plantar Rat Hindpaw One Day After an Incision," J Neurophysiol, 2002, 87:721-731, 11 pgs.
Pu, S-F, et al., "Insulin-Like Growth Factor-II Increases and IGF Is Required for Postnatal Rat Spinal Motoneuron Survival Following Sciatic Nerve Axotomy," J Neurosci Res, 1999, 55:9-16, 8 pgs.
Reynolds, M.L., et al., "Decreased Skin Sensory Innervation in Transgenic Mice Overexpressing Insulin-Like Growth Factor-II," Neuroscience, 1997, 79(3):789-97, 9 pgs.
Rhodin, A., et al., "Recombinant human growth hormone improves cognitive capacity in a pain patient exposed to chronic opioids," Acta Anaesthesiol Scand, 2014, 58:759-765, 7 pgs.
Ririe, D.G., et al., "Age-dependent Responses to Thermal Hyperalgesia and Mechanical Allodynia in a Rat Model of Acute Postoperative Pain," Anesthesiology, 2003, 99:443-48, 6 pgs.
Ritter, A.M., et al., "Maturation of Cutaneous Sensory Neurons From Normal and NGF-Overexpressing Mice," J Neurophysiol, 2000, 83:1722-1732, 11 pgs.
Ritter, A.M., et al., "Requirement for nerve growth factor in the development of myelinated nociceptors in vivo," Nature, 1991, 350:500-502, 3 pgs.
Rosenfeld, R.G., et al., "The Growth Hormone Cascade and Its Role in Mammalian Growth," Horm Res, 2009, 71(Suppl 2):36-40, 5 pgs.
Ross, J.L., et al., "Muscle IL1β Drives Ischemic Myalgia via ASIC3-Mediated Sensory Neuron Sensitization," J Neurosci, 2016, 36(26):6857-6871, 15 pgs.
Ross, J.L., et al., "Sensitization of group III and IV muscle afferents in the mouse after ischemia and reperfusion injury," J Pain, Dec. 2014, 15(12):1257-70, 27 pgs.
Salomon, Md, F., et al., "The Effects of Treatment with Recombinant Human Growth Hormone on Body Composition and Metabo-

(56) References Cited

OTHER PUBLICATIONS lism in Adults with Growth Hormone Deficiency," The New England Journal of Medicine, Dec. 1989, 321(26):1797-1803, 8 pgs.
Schwaller, M.Sc., F., et al., "Targeting p38 Mitogen-activated Protein Kinase to Reduce the Impact of Neonatal Microglial Priming on Incision-induced Hyperalgesia in the Adult Rat," Anesthesiology, Jun. 2015, 122(6): 1377-90, 14 pgs.
Shim, B., et al., "Mechanical and Heat Sensitization of Cutaneous Nociceptors in Rats with Experimental Peripheral Neuropathy," Neuroscience, 2005, 132:193-201, 9 pgs.
Sonntag, W.E., et al., "Diverse Roles of Growth Hormone and Insulin-Like Growth Factor-1 in Mammalian Aging: Progress and Controversies," J Gerontol A Biol Sci Med Sci, Jun. 2012, 67A(6):587-598, 12 pgs.
Souza, F.M., et al., "Adverse effects of growth hormone replacement therapy in children," Arq Bras Endocrinol Metabol, 2011, 55:559-565, 7 pgs.
Talhouk, R.S., et al., "Growth hormone releasing hormone reverses endotoxin-induced localized inflammatory hyperalgesia without reducing the upregulated cytokines, nerve growth factor and gelatinase activity," Prog Neuro-Psychopharmacology Biol. Psychiatry, 2004, 28:625-631, 7 pgs.
Torsney, C., et al., "Age-Dependent Effects of Peripheral Inflammation on the Electrophysiological Properties of Neonatal Rat Dorsal Horn Neurons," J Neurophysiol, 2002, 87:1311-7, 7 pgs.
Valdés, J.A., et al., "IGF-1 Induces $IP_3$-Dependent Calcium Signal Involved in the Regulation of Myostatin Gene Expression Mediated by NFAT During Myoblast Differentiation," Journal of Cellular Physiology, 2012, 1452-1463, 12 pgs.
Varco-Merth, B., et al., "Differential effects of STAT proteins on growth hormone-mediated IGF-I gene expression," Am J Physiol Endocrinol Metab, 2014, 307:E847-55, 9 pgs.
Walker, S.M., et al., "Neonatal inflammation and primary afferent terminal plasticity in the rat dorsal horn," Pain, 2003, 105:185-195, 11 pgs.
Walker, S.M., et al., "Persistent changes in peripheral and spinal nociceptive processing after early tissue injury," Exp Neurol, Jan. 2016, 275(2 0):253-60, 18 pgs.
Waters, M.J., et al., "New insights into growth hormone action," J Mol Endocrinol, 2006, 36:1-7, 7 pgs.
Xu, MD, J., et al., "Guarding Pain and Spontaneous Activity of Nociceptors after Skin versus Skin Plus Deep Tissue Incision, " Anesthesiology, 2010, 112:153-64, 12 pgs.
Ye, Y., et al., "Early Postnatal Loss of Heat Sensitivity Among Cutaneous Myelinated Nociceptors in Swiss-Webster Mice," J Neurophysiol, 2010, 103:1385-1396, 12 pgs.
Yu, Z-B, et al., "Transcutaneous bilirubin nomogram for predicting neonatal hyperbilirubinemia in healthy term and late-preterm Chinese infants," Eur J Pediatr, 2011, 170:185-91, 8 pgs.
Zhang, C., et al., "Myocardial ischemic nociceptive signaling mediated by $P2X_3$ receptor in rat stellate ganglion neurons," Brain Res Bull, 2008, 75:77-82, 6 pgs.
Zhang, Y., et al., "Peripheral pain is enhanced by insulin-like growth factor 1 through a G protein-mediated stimulation of T-type calcium channels," Sci Signal, Oct. 2014, 7(346):ra94, 16 pgs.
Zheng, W-H, et al., "Insulin-like growth factor-1 (IGF-1) induces the activation/phosphorylation of Akt kinase and cAMP response element-binding protein (CREB) by activating different signaling pathways in PC12 cells," BMC Neurosci, 2006, 7:51, 10 pgs.

COMPOSITIONS AND METHODS FOR TREATMENT OF CUTANEOUS OR MUSCLE INCISION PAIN

CROSS REFERENCE TO RELATED APPLICATIONS

This application is a continuation of U.S. application Ser. No. 16/180,085, filed Nov. 5, 2018, which is a continuation of U.S. application Ser. No. 15/349,651, filed Nov. 11, 2016, which claims priority to and benefit of U.S. Provisional Application Ser. No. 62/262,594 filed Dec. 3, 2015 entitled "Growth Hormone to Treat Pediatric Pain" the contents of which are incorporated herein in their entirety for all purposes.

GOVERNMENT SUPPORT CLAUSE

This invention was made with government support under HD077483 and NS103179 awarded by the National Institutes of Health. The government has certain rights in the invention.

Reference to Sequence Listing

A Sequence Listing submitted as an ASCII text file via EFS-Web is hereby incorporated by reference in accordance with 35 U.S.C. § 1.52(e). The name of the ASCII text file for the Sequence Listing is Seq_List_16985274_ST25.txt, the date of the creation of the ASCII text file is Aug. 26, 2020, and the size of the ASCII text file is 3.30 KB.

BACKGROUND

It has been reported that pain is most often the principal reason for pediatric patients to seek medical treatment. Pain management in children is a significant clinical problem. Post-operative pain or surgical pain is one type of pain that is sometimes undertreated to avoid potentially harmful side effects of analgesics in neonates after surgery. Chronic pain is anothertype of pain that also affects a significant amount of the pediatric population (15%-20%), and which imposes a substantial monetary burden on patients, families, and caregivers. Persistent changes in nociceptive processing occur as a result of early life injury specifically, and results from a "priming" effect due to the early injury and resulting pain.

Many of the pain therapies used in children such as opioids, for example, can not only be inadequate for pain relief, but also have inter-patient variability in clinical responses and can often produce significant adverse effects including nausea, vomiting, and respiratory depression (RD) in as many as 50% of pediatric patients and have been linked to the disrupted development of language skills, social behaviors and attention Usage of opioids or anti-inflammatories in utero have been linked to the improper development of language skills, social behaviors and attention, suggesting that such use should be limited or avoided entirely Thus, side effects often overshadow the analgesia desired from delivering these pharmacotherapies to children. Further, there is currently no efforts to avoid the long term consequences of pain in adulthood that results from priming as a result of pain early in life, which is not prevented using standard pain management therapies.

Hence, the development of more suitable pediatric pain therapies devoid of these adverse effects is of vital importance. However, to date, most analgesic development has been evolutionary, with refinements in compounds directed against well-known targets. Better drugs are clearly needed, but new targets for therapy must be determined before superior compounds can be developed.

The instant application seeks to address one or more of these needs in the art.

BRIEF SUMMARY

Disclosed are methods of treating pain in a mammal, which may include the step of administering human growth hormone to a mammal in need thereof. The pain treated by the disclosed methods may be of a type caused by inflammation induced mechanical and/or thermal hypersensitivity, and may include, for example, a pain type resulting from one or more conditions selected from peripheral injury pain, post-operative pain, cutaneous inflammation, cutaneous incision, muscle incision, or chronic pain. Disease states in which the disclosed methods may be used include fibromyalgia, sickle cell anemia, epidermolysis bullosa, erythromelalgia, complex regional pain syndrome, or generalized muscle pain.

DETAILED DESCRIPTION

Definitions

Figure 1:
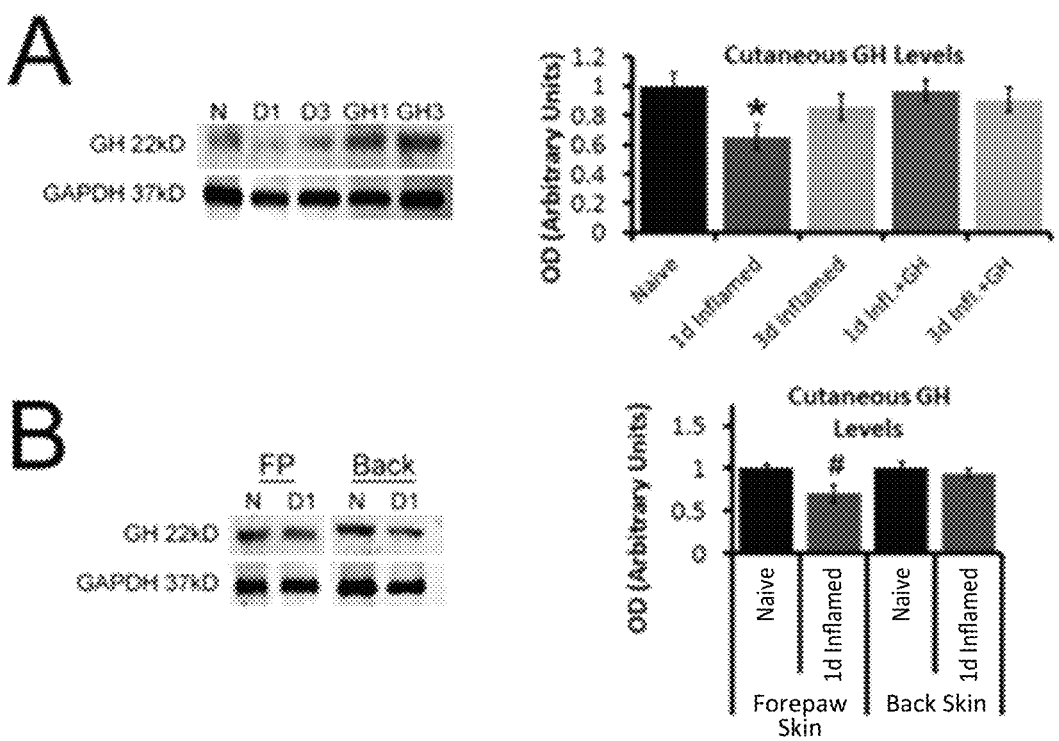
FIG. 1: Cutaneous GH protein expression with or without exogenous GH delivery after hairy skin inflammation at P14. Panel A: At P14, GH was found to be significantly reduced in the inflamed hairy hindpaw skin ld after peripheral injury. Levels in the inflamed area were reduced 35% (±9%) relative to that observed in naïve hairy skin, but returned to naïve levels by day 3 (D3). Treatment of mice with exogenous GH for three days prior to injury was able to block the reduction in GH levels found after cutaneous inflammation. Panel B: Analysis of naïve forepaw (FP) or back skin, or cutaneous tissue from these same regions obtained from mice ld post carrageenan injection into the hairy hindpaw skin at P14, showed no differences in GH levels. The decrease in GH expression that was found in the FP skin after hindpaw skin inflammation, was determined to be a 29% (±10%) reduction, but this was not found to be statistically significant vs. naïve FP skin. n=3-4/group, * $p<0.05$ vs. naïve, # $p<0.07$ vs. naive; One-way ANOVA/ Tukey's post hoc.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms and expressions used herein have the ordinary meaning as is accorded to such terms and expressions with respect to their corresponding respective areas of inquiry and study except where specific meanings have otherwise been set forth herein.

As used herein and in the appended claims, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the art. Alternatively, "about" can mean a range of up to 20%, or up to 10%, or up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The terms "individual," "host," "subject," and "patient" are used interchangeably to refer to an animal that is the object of treatment, observation and/or experiment. Generally, the term refers to a human patient, but the methods and compositions may be equally applicable to non-human subjects such as other mammals. In some embodiments, the terms refer to humans. In further embodiments, the terms may refer to children.

The terms "neonate" and "neonatal" are intended to refer to infants up to one year of age.

As used herein, the term "child" means a mammal one year of age to 13 years of age.

As used herein, "juvenile" refers to a mammal of 13 years of age to eighteen years of age.

As used herein, the term young or early adult refers to a mammal of from 18 years of age to 40 years of age.

As used herein, the term adult refers to a mammal greater than 40 years of age.

"Therapeutically effective amount" relates to the amount or dose of an active compound or composition described herein that will lead to one or more therapeutic effect, in particular desired beneficial effects. A therapeutically effective amount of a substance can vary according to factors such as the disease state, age, sex, and weight of the subject, and the ability of the substance to elicit a desired response in the subject. Dosage regime may be adjusted to provide the optimum therapeutic response. For example, several divided doses may be administered daily or the dose may be proportionally reduced as indicated by the exigencies of the therapeutic situation.

The phrase "pharmaceutically acceptable," as used in connection with compositions of the disclosure, refers to molecular entities and other ingredients of such compositions that are physiologically tolerable and do not typically produce untoward reactions when administered to a subject (e.g., human). In certain embodiments, as used herein, the term "pharmaceutically acceptable" means approved by a regulatory agency of a Federal or a state government or listed in the U.S. Pharmacopeia or other generally recognized pharmacopeia for use in mammals (e.g., humans).

The term "carrier" applied to pharmaceutical compositions of the disclosure refers to a diluent, excipient, or vehicle with which an active compound (e.g., dextromethorphan) is administered. Such pharmaceutical carriers can be sterile liquids, such as water, saline solutions, aqueous dextrose solutions, aqueous glycerol solutions, and oils, including those of petroleum, animal, vegetable, or synthetic origin, such as peanut oil, soybean oil, mineral oil, sesame oil and the like. Suitable pharmaceutical carriers are described in "Remington's Pharmaceutical Sciences" by E. W. Martin, 18th Edition.

Applicants have found that GH treatment may be a clinically effective pain therapy in patients, in particular in the developing human, including neonates, children, and juveniles, however, at the doses currently used to stimulate growth in growth hormone deficiency (GHD), GH would not be suitable to use in normal children due to metabolic and other potential side effects. To date, no studies have analyzed the specific effects of GH on cutaneous or muscle sensory neurons or the observed hyper sensitivity after injury in neonates. The void in pediatric pain research in general further hinders the ability to identify new therapies for pediatric post-surgical pain that could target the appropriate peripheral receptors or primary afferents that are driving pain development in children. Although a few studies have analyzed the behavior effects of GH-related pathways on pain in rodents, these few studies have all been performed in adults, which cannot be easily extrapolated to neonates. Thus, pediatric post-operative pain development is quite understudied compared to adult pain. Applicant has found that GH treatment in neonate mice with cutaneous inflammation or cutaneous or muscle incision appears to block the injury induced alterations in primary sensory neurons in addition to behavioral hypersensitivity through an IGFr1 dependent mechanism. Without intending to be limited by theory, the analgesic effect of GH I treatment appears to be due to the fact that peripheral injury in a neonate establishes a localized "GH deficient" state in the injured skin or muscle, and supplementing the animal with exogenous GH reverses this state, subsequently leading to a restoration of primary afferent function and behavior. This may be due to GH tonically reducing the expression of serum response factor (SRF) which can regulate IGFr1 transcription in sensory neurons. GH treatment at the time of neonatal insult was also found to blunt the priming effects of a tissue or muscle injury on the hypersensitivity to subsequent re-injury later in life.

Figure 19:
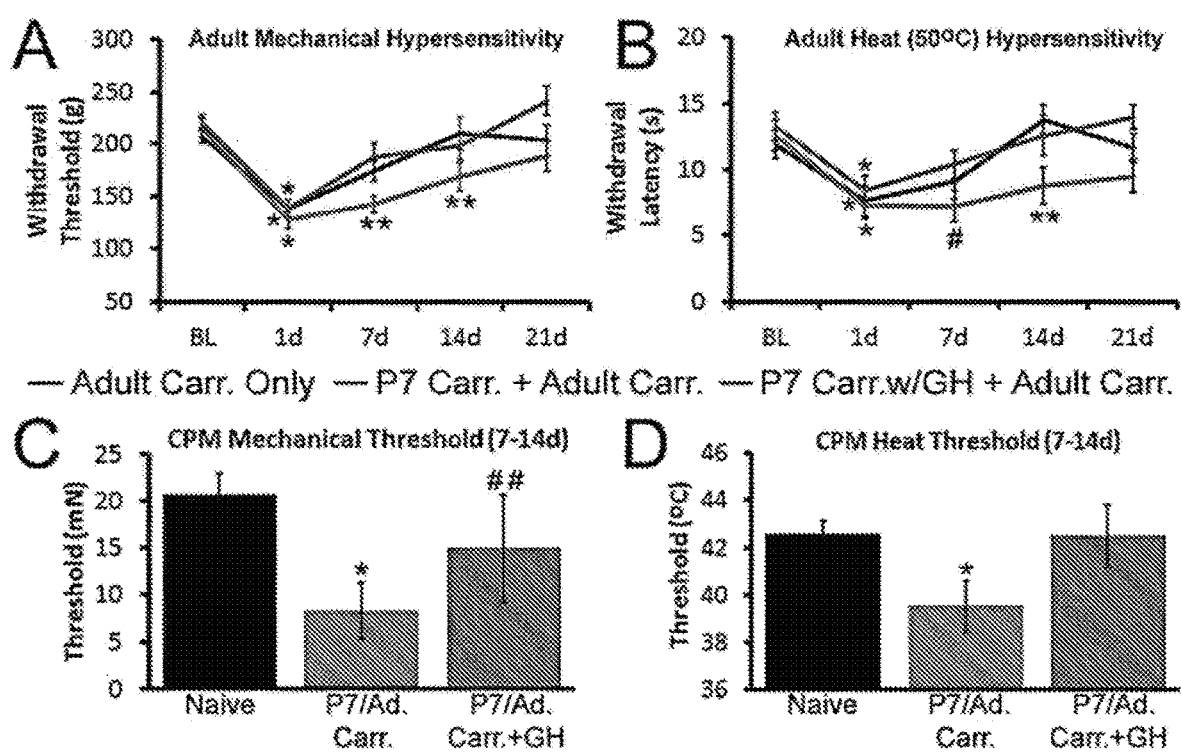
FIG. 19. Priming effects of neonatal inflammation on young adult responses to inflammatory insult with or without neonatal GH treatment. Cutaneous inflammation at P7 prolongs the mechanical (Randall-Selitto; A) and heat (water bath; B) hypersensitivity observed in young adult mice injected with carrageenan at P35. Treatment of these mice with GH at P7 however, blunts this priming effect (n=8-12ea). Polymodal C-fiber (CPM) afferents in young adult mice (Naïve, n=66; P7/Ad Can, n=17; P7/Ad Carr+GH, n=18) with hairy skin carrageenan injection at P7 and P35 display decreased mechanical (C) and heat (D) thresholds at 7-14d (combined) post inflammation vs. naives. A GH treatment at P7 blunts these effects on afferents. *p<0.05 vs BL or naive; **p<0.05 vs BL and other time matched groups; <0.05 vs BL but no other groups; ##not different than naïve or P7/Ad Carr.; RM or 1-way ANOVA/Holm Sidak. Mean±SEM.

Peripheral sensitization occurs after injury at all ages, but insults sustained during development have the potential to be much more detrimental to the long-term outcomes of neonates. The neonatal period is a critical stage for the structural and functional reorganization of the sensory system. For example, there is a known switch in neurotrophic factor sensitivity during the first week of life, whereby sensory neurons downregulate trkA and upregulate c-ret rendering them responsive to glial cell line-derived neurotrophic factor (GDNF) instead of nerve growth factor (NGF). This switch subsequently regulates how the sensory neurons relay information from the periphery to the spinal dorsal horn (DH). Applicant has found that a single GH treatment during early life insult prevents the known priming effects of such injuries on later life hypersensitivity to subsequent re-injury. Results indicate that young adult mice with cutaneous inflammation display a longer lasting hypersensitivity to mechanical and thermal stimuli if they experience an early life injury (P7 inflammation) compared to mike that only received carrageenan as adults. Deliver of GH 1.5 mg/kg, ip. 1×, to neonates at the time of neonatal inflammation (no pre-treatment) was able to significantly block this priming effect in the older mice during inflammation in addition to blunting the late stage CPM neuron sensitization observed in mice with dual injury. FIG. 19.

Cutaneous inflammation alters the function of primary afferents and gene expression in the affected dorsal root ganglia (DRGs). However specific mechanisms of injury-induced peripheral afferent sensitization and behavioral hypersensitivity during development are not fully understood. To determine if GH played a role in modulating sensory neuron function and hyper-responsiveness during skin inflammation in young mice, Applicant examined behavioral hypersensitivity and the response properties of cutaneous afferents using an ex vivo hairy skin-saphenous nerve-dorsal root ganglion (DRG)-spinal cord preparation.

The appropriate interaction between primary afferents and the spinal cord during development is necessary for establishing normal responsiveness to external stimuli. Injury during early life however, has been shown to alter DH neuron development, which can induce altered behavioral responsiveness to thermal and mechanical stimuli in adulthood. It has been hypothesized that this phenomenon is due to altered peripheral A-fiber sensitization along with improper development of glycinergic inhibition; a notion that was recently supported by Applicant. As previously reported, Applicant also found that developing cutaneous nociceptors were sensitized to heat and mechanical stimuli in a pattern that differed from adults.

It has been shown that patients with growth hormone deficiency (GHD), along with showing deficits in growth, can also display resting pain. Applicant and others have found that GH treatment is clinically effective pain therapy in these children and in a small subpopulation of adult patients. (Cimaz, R., Rusconi, R., Fossali, E. & Careddu, P. Unexpected healing of cutaneous ulcers in a short child. *Lancet* 358, 211-212, doi:10.1016/S0140-6736(01)05413-7 (2001); Nathan, A., Rose, J. B., Guite, J. W., Hehir, D. & Milovcich, K. Primary erythromelalgia in a child responding to intravenous lidocaine and oral mexiletine treatment. *Pediatrics* 115, e504-507, doi:10.1542/peds.2004-1395 (2005); Cuatrecasas G., Gonzalez M J, Alegre C, Sesmilo G, Fernandez-Sola J, Casanueva F F, Garcia-Fructuoso F, Poca-Diaz V, Izquierdo JP, Puig-Domingo M. High prevalence of growth hormone deficiency in severe fibromyalgia syndromes. J. Clin. Endocrin. Metab. 95: 4331-37. (2010); Cuatrecasas Gu., Alegre C, Fernandez-Sola J, Gonzalez MJ, Garcia-Fructuoso F, Poca-Diaz V, Nadal A, Cuatrecasas Ga., Navarro F, Mera, A, Lage M, Peino R, Casanueva F, Linan C, Sesmilo G, Coves M J, Izquierdo J P, ALvarez I, Granados E, Puig-Domingo M. Growth hormone treatment for sustained pain reduction and improvement in quality of life in severe fibromyalgia. Pain. 153: 1382-89. (2012).). GH plays important roles in homeostasis and tissue repair after injury in addition to its growth promoting effects in children. However, GH-related signaling molecules such as GH release hormone (GHRH) and ghrelin have been found to decrease mechanical and thermal hypersensitivity after inflammation in adult rodents. In addition, recent human studies have showed that GH treatment provides analgesia in a subpopulation of adult patients with fibromyalgia.

Disclosed herein are methods of treating pain in a mammal. The methods may comprise the step of administering human growth hormone to a mammal in need thereof. In one aspect, the mammal may be selected from a human neonate, a human child, a human juvenile, a human young adult, or a human adult. In one aspect, the developing mammal does not have a systemic growth hormone deficiency.

In one aspect, the pain may be caused by inflammation induced mechanical and/or thermal hypersensitivity.

In one aspect, the human growth hormone may be administered to a mammal in an amount effective to treat a pain type resulting from one or more conditions selected from peripheral injury pain, post-operative pain, cutaneous inflammation, cutaneous incision, muscle incision, or chronic pain.

In one aspect, the human growth hormone may be administered to treat pain associated with a disease or condition selected from fibromyalgia, sickle cell anemia, epidermolysis bullosa, erythromelalgia, complex regional pain syndrome, or generalized muscle pain.

In one aspect, the growth hormone may be administered post-operatively.

In one aspect, the growth hormone may be administered at a dose of from about 0.1 mg/kg to about 2.5 mg/kg, or from about 1 mg/kg to about 1.5 mg/kg.

In one aspect, the human growth hormone may be administered at a time period selected from prior to an event likely to result in pain, at the time of the event likely to cause pain, or following an event likely to cause pain, or a combination thereof In one aspect, the administration step may occur prior to an event likely to cause pain. The administration may occur at a time period selected from about one day prior to the event, about two days prior to the event, or about three days prior to the event.

In one aspect, the dose may be administered systemically. The dose may be administered over a period of from 1 to 5 days, or 2 to 3 days. Where the dose is administered in a single day, the dose may be from about 0.3 mg/kg to about 6 mg/kg, or from about 0.5 to about 5 mg/kg, or about 1.0 to about 4 mg/kg, or about 2.0 to about 3 mg/kg.

In one aspect, the growth hormone may be administered topically at a dose of from about 0.1 mg/kg to about 3 mg/kg, or from about 1 mg/kg to about 2 mg/kg, or from about 0.5 to about 1 mg/kg.

In one aspect, the human growth hormone may be administered to the site of cutaneous and/or muscular inflammation.

In one aspect, the administration may be in an amount that avoids a side effect of human growth hormone administration typically associated with treatment at higher levels for treatment of human growth hormone deficiency or short stature, wherein the side effect is selected from weight gain, transient fevers, hyperglycemia, or combinations thereof In one aspect, the administration of growth hormone may prevent acute to chronic pain transition. Acute to chronic pain transition is a long term priming effect of an injury during development of a developing mammal to a subsequent re-injury as a young adult or adult. In this aspect, the administration of human growth hormone during a neonatal injury may prevent altered DH neuron development and altered behavioral responsiveness to thermal and mechanical stimuli in adulthood.

In one aspect, a method of preventing transition from acute to chronic inflammatory pain in a human subject is disclosed. In this aspect, the method may comprise the step of administering human growth hormone to a subject immediately prior, during, or after an event likely to cause pain.

In one aspect, a kit is disclosed. The kit may comprise a composition comprising human growth hormone, and a means for delivery of the composition to a human in need thereof.

In one aspect, an article of manufacture is disclosed. The article of manufacture may comprise, for example, a container comprising a label and a composition comprising growth hormone. The label may indicate that the composition is to be administered to a neonate, child, juvenile, or young adult, having, suspected of having, or at risk for developing, pain. The pain may include any one or more types of pain disclosed herein. In one aspect, the pain may be of a type that results from one or more of cutaneous inflammation, cutaneous incision, or muscle incision. In one aspect, the label may further indicate that the composition is to be administered to a neonate, child, juvenile, or young adult during, after, or prior to an event likely to cause pain resulting from one or more of cutaneous inflammation, cutaneous incision, or muscle incision, at a time period selected from at least one day prior, at least two days prior, or at least three days prior to said event.

Dosage

As will be apparent to those skilled in the art, dosages outside of these disclosed ranges may be administered in some cases. Further, it is noted that the ordinary skilled clinician or treating physician will know how and when to interrupt, adjust, or terminate therapy in consideration of individual patient response.

In certain embodiment, the dosage of human growth hormone, based on weight of the active compound, administered to prevent, treat, manage, or ameliorate pain in a subject may be about 0.25 mg/kg, 0.5 mg/kg, 0.1 mg/kg, 1 mg/kg, 2 mg/kg, 3 mg/kg, 4 mg/kg, 5 mg/kg, 6 mg/kg, or more of a subject's body weight. In another embodiment, the dosage of human growth hormone to prevent, treat, manage, or ameliorate pain in a subject is a unit dose of about 0.1 mg to 200 mg, 0.1 mg to 100 mg, 0.1 mg to 50 mg, 0.1 mg to 25 mg, 0.1 mg to 20 mg, 0.1 mg to 15 mg, 0.1 mg to 10 mg, 0.1 mg to 7.5 mg, 0.1 mg to 5 mg, 0.1 to 2.5 mg, 0.25 mg to 20 mg, 0.25 mg to 15 mg, 0.25 to 12 mg, 0.25 to 10 mg, 0.25 mg to 7.5 mg, 0.25 mg to 5 mg, 0.5 mg to 2.5 mg, 1 mg to 20 mg, 1 mg to 15 mg, 1 mg to 12 mg, 1 mg to 10 mg, 1 mg to 7.5 mg, 1 mg to 5 mg, or 1 mg to 2.5 mg.

In one aspect, human growth hormone may be present in an amount of from about 0.5% to about 95%, or from about 1% to about 90%, or from about 2% to about 85%, or from about 3% to about 80%, or from about 4%, about 75%, or from about 5% to about 70%, or from about 6%, about 65%, or from about 7% to about 60%, or from about 8% to about 55%, or from about 9% to about 50%, or from about 10% to about 40%, by weight of the composition.

The compositions may be administered in oral dosage forms such as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular forms all utilizing dosage forms well known to those of ordinary skill in the pharmaceutical arts. The compositions may be administered by intranasal route via topical use of suitable intranasal vehicles, or via a transdermal route, for example using conventional transdermal skin patches. A dosage protocol for administration using a transdermal delivery system may be continuous rather than intermittent throughout the dosage regimen.

A dosage regimen will vary depending upon known factors such as the pharmacodynamic characteristics of the agents and their mode and route of administration; the species, age, sex, health, medical condition, and weight of the patient, the nature and extent of the symptoms, the kind of concurrent treatment, the frequency of treatment, the route of administration, the renal and hepatic function of the patient, and the desired effect. The effective amount of a drug required to prevent, counter, or arrest progression of pain can be readily determined by an ordinarily skilled physician The pharmaceutical compositions may include suitable dosage forms for oral, parenteral (including subcutaneous, intramuscular, intradermal and intravenous), transdermal, sublingual, bronchial or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. Oral preparations include push-fit capsules made of gelatin, as well as soft, scaled capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. For topical or nasal administration, penetrants or permeation agents that are appropriate to the particular barrier to be permeated are used in the formulation. Such penetrants are generally known in the art. The pharmaceutical compositions are prepared by conventional techniques appropriate to the desired preparation containing appropriate amounts of the active ingredient, that is, one or more of the disclosed active agents or a pharmaceutically acceptable salt thereof according to the invention.

The dosage of growth hormone used to achieve a therapeutic effect will depend not only on such factors as the age, weight and sex of the patient and mode of administration, but also on the degree of inhibition desired and the potency of human growth hormone for the particular disorder or disease concerned. It is also contemplated that the treatment and dosage of human growth hormone may be administered in unit dosage form and that the unit dosage form would be adjusted accordingly by one skilled in the art to reflect the relative level of activity. The decision as to the particular dosage to be employed (and the number of times to be administered per day) is within the discretion of the physician, and may be varied by titration of the dosage to the particular circumstances of this invention to produce the desired therapeutic effect.

EXAMPLES

GH exerts much of its effects through insulin-like growth factor (IGF)/IGF receptor (IGFr) signaling, but does not bind IGFr directly. IGF-1 synthesis has been shown to increase after tissue injuries and locally produced IGF-1 has been linked to the development of injury-induced hypersensitivity. Moreover, IGFr1 antagonists block mechanical and thermal hyper-responsiveness during inflammation in adults. Applicant hypothesized that GH signaling may also play an important role in pain modulation during postnatal development. Nevertheless, the role of GH in the development of neonatal pain remains unclear. In the current study, Applicant tested the hypothesis that a reduction in GH levels during neonatal cutaneous inflammation drives the sensitization of primary afferents and pain-related hypersensitivity possibly by suppressing afferent specific IGFr1 upregulation within sensory neurons.

Example 1

Materials and Methods

Animals. Male and female Swiss Webster mice (Charles River) from postnatal day 6 through 21 (±~0.5 d around the specified age) were used in these studies. All animals were housed with the mother, which was provided food and water ad libitum and maintained on a 12-hour light/dark cycle. All procedures were approved by the Institutional Animal Care and Use Committee at Cincinnati Children's Hospital Medical Center, under AAALAC approved practices. No differences between male and female mice were detected for any tests described below and thus data was combined from both sexes throughout the manuscript. As Applicant has documented age-related effects of injury on the excitability of primary afferent neurons, Applicant assessed the effects of cutaneous inflammation beginning at two different postnatal ages (P7 or P14) in order to account for any potential developmental effects (Jankowski M P, Ross J L, Weber J D, Lee F B, Shank A T, Hudgins R C. Age-dependent sensitization of cutaneous nociceptors during developmental inflammation. Mol Pain 2014; 10:34. doi:10.1186/1744-8069-10-34).

Incision Model

Skin plus muscle incisions: Skin plus muscle incisions will follow a modified version of Xu and Brennan (Xu J, Brennan T J. Guarding pain and spontaneous activity of nociceptors after skin plus deep tissue incision. Anesthesiology. 112, 153-64. (2010).). Here however, we will perform the incisions from the hairy skin side of the hindpaw through to the flexor digitorum brevis muscles. Visualization of the incision site is performed during terminal experiments to verify that the main branch of the saphenous nerve is not axotomized. Incisions are made from the hairy side of the paw so that the correct mechanical sensitivity tests for neonates may be performed and because cutaneous afferents are being analyzed with a hairy skin ex vivo preparation (Xu J, Brennan T J. Guarding pain and spontaneous activity of nociceptors after skin plus deep tissue incision. Anesthesiology. 112, 153-64. (2010).)

Muscle Pain-Related Behavioral Assessments

To then assess pain-related behaviors in other cohorts, a number of recognized measures for neonates is used. These tests include: assessment of ongoing/spontaneous pain, which employs a modified version of guarding behaviors as outlined in Xu and Brennan (Xu J, Brennan T J. Guarding pain and spontaneous activity of nociceptors after skin plus deep tissue incision. Anesthesiology. 112, 153-64. (2010). In this model, an additional measure of guarding can be detected specifically in neonates by monitoring upward toe curling (not shown). Hairy skin can be stimulated using an increasing series of von Frey filaments (0.07 g-6 g) to assess mechanical responsiveness (withdrawal threshold), followed by immersion of the hindpaws in a hot or cold water bath of varying temperatures (38-50° C. or 0-10° C., respectively) to assess heat and cold sensitivity (withdrawal latency) (Marsh, D., Dickenson, A., Hatch, D. & Fitzgerald, M. Epidural opioid analgesia in infant rats I: mechanical and heat responses. Pain 82, 23-32 (1999). Fitzgerald, M., Shaw, A. & MacIntosh, N. Postnatal development of the cutaneous flexor reflex: comparative study of preterm infants and newborn rat pups. Developmental medicine and child neurology 30, 520-526 (1988).). Von Frey stimulation of the hairy skin is used because it is known that stimulation of the plantar surface can lift the paw of neonates, which confounds the results of these mechanical tests. Finally, mice >P14 will also be assessed for grip strength using a grip strength meter. These are all sound methods to assess somatosensation in neonatal rodents.

Carrageenan-induced inflammation. Mice are anesthetized under 3% isofluorane and 3-10 µL of 3% carrageenan (in 0.9% NaCl) is injected into the right hairy hindpaw skin by using a 30 gauge needle with syringe according to previous procedures (Jankowski M P, Ross J L, Weber J D, Lee F B, Shank A T, Hudgins R C. Age-dependent sensitization of cutaneous nociceptors during developmental inflammation. Mol Pain 2014; 10:34. doi:10.1186/1744-8069-10-34.). The carrageenan was expelled beginning at the ankle and allowed to fill under the hairy hindpaw skin towards the digits. Injections were directed towards the medial side of the hindpaw in order to target the saphenous nerve field as accurately as possible. 1 µL/g body weight was used as a guide for these injections according to previous studies (Torsney C, Fitzgerald M. Age-dependent effects of peripheral inflammation on the electrophysiological properties of neonatal rat dorsal horn neurons. J. Neurophysiol. 2002;87:1311-7. Available: http://jn.physiology.org/content/87/3/1311.abstract. Accessed 23 Oct. 2015.) in order to account for subtle variations in paw size that occurs as a mouse develops during this period of life. At P7, mice are approximately three to four grams in total body weight, while mice at P14 are around seven to eight grams. Using the abovementioned guide, within a given age group, only variations of approximately 1 µL were made. GH treatments did not alter injection volumes within a given age group. Regardless, ipsilateral and contralateral hindpaw edema was measured using calipers to ensure that a similar degree of inflammation was attained at the different ages. All behavioral, electrophysiological, anatomical or molecular analyses were performed 1d, 3d and 7d after injection of carrageenan and compared to un-anesthetized naïve mice at P7 or P14, or with each other.

Growth hormone treatments and side effects analysis. Mouse recombinant growth hormone (GH; GenScript) is diluted in $H_2O$ (50 µL) in different concentrations (0.1 mg/kg-0.5 mg/kg) and intraperitoneally injected once per day beginning three days prior to, or once on the day of carrageenan injections or incision at P7 or P14 as indicated above. The initial guide that was used for this injection strategy was based on the amount of GH that would be needed to begin modulating systemic GH-mediated signaling without concurrently stimulating growth (Farris G M, Miller G K, Wollenberg G K, Molon-Noblot S, Chan C, Prahalada S. Recombinant rat and mouse growth hormones: risk assessment of carcinogenic potential in 2-year bioassays in rats and mice. Toxicol. Sci. 2007; 97:548-61. doi:10.1093/toxsci/kfm059.). The maximum serum concentration of GH detected from this injection regimen in rodents would only reach approximately 100-150 ng/mL, three hours after the final injection. By 24 hours after the final dose however, which is when post inflammation assessments are performed, systemic GH levels should return to normal concentrations (~0-20 ng/mL). Body weight, temperature and urine ketones were monitored to determine potential side effects of GH administration. Temperature was determined on the thorax using a contact thermocouple connected to a temperature readout device according to previous procedures (Goodrich C A. Measurement of body temperature in neonatal mice. J. Appl. Physiol. 1977; 43:1102-5. Available: http://www.ncbi.nlm.nih.gov/pubmed/606696.). Levels of ketones in the urine were determined by applying a small droplet of urine to the testing end of a Ketodiastix (Bayer) and verifying ketone concentration according to the color coded scale provided by the manufacturer.

siRNA production and in vivo nerve injections. Mice are anesthetized as described above. A small incision is made in the mid-thigh region exposing the saphenous nerve. The nerve is loosened from the adjacent connective tissue and placed onto a parafilm platform. Then 0.05-0.1 µL of 20 uM non-targeting control (siCON) or IGFr1 targeting (siIGFr1) siRNAs (Thermo Scientific) is pressure injected into the saphenous nerve using a quartz microelectrode connected to a pico-spritzer. The control siRNAs used were a pool of four non-targeting duplexes that do not target any gene in the mouse genome (Thermo). The targeting sequences used to design each siCON duplex are as follows: 5'-UAAGGC-UAUGAAGAGAUAC-3' (SEQ ID NO:1), 5'-AU-GUAUUGGCCUGUAUUAG-3'(SEQ ID NO:2), 5'-AUGAACGUGAAUUGCUCAA-3'(SEQ ID NO:3), 5'-UGGUUUACUGUCGACUAA-3'(SEQ ID NO:4). The specific targeting sequence for IGFr1 used for in vivo studies was determined by selecting four different targeting sequences (Thermo Scientific; Cat#D-056843) and transfecting Neuro2A cells in vitro according to previous reports (Jankowski M P, Cornuet P K, McIlwrath S, Koerber H R, Albers K M. SRY-box containing gene 11 (Sox11) transcription factor is required for neuron survival and neurite growth. Neuroscience 2006; 143:501-514.) with the individual IGFr1 targeting siRNAs (1-4) and comparing them to untreated cells or those transfected with the non-targeting control siRNAs (siCON). RNA is isolated from the different culture conditions, reverse transcribed and cDNAs were used in SYBR Green realtime PCR reactions as described below. The most efficiently targeting siRNA (Sequence #1: 5'-CCAUCGAGGUUACUAAUGA-3' (SEQ ID NO:5)) was used thereafter for this report. After injections, the incision is closed with a 7-0 silk suture. For P7 mice, siRNAs are injected one day before inflammation or incision, and for P14 mice, siRNAs are injected two days before inflammation or incision. This strategy follows a modified version of previous reports (Jankowski M P, McIlwrath S L, Jing X, Cornuet P K, Salerno K M, Koerber H R, Albers K M. Sox1 1 transcription factor modulates peripheral nerve regeneration in adult mice. Brain Res. 2009; 1256:43-54. doi:10.1016/j.brainres.2008.12.032.; Jankowski M P, Rau K K, Soneji D J, Anderson C E, Koerber H R. Enhanced artemin/GFRa3 levels regulate mechanically insensitive, heat-sensitive C-fiber recruitment after axotomy and regeneration. J. Neurosci. 2010; 30:16272-16283; Jankowski M P, Rau K K, Soneji D J, Ekmann K M, Anderson C E, Molliver D C, Koerber H R. Purinergic receptor P2Y1 regulates polymodal C-fiber thermal thresholds and sensory neuron phenotypic switching during peripheral inflammation. Pain 2012; 153:410-419. doi:10.1016/j.pain.2011.10.042.).

Behavioral analyses. All behavioral experiments were performed in which the experimenter was blinded to the various conditions. siCON injected control mice that did not receive carrageenan injections, were performed separately by a different experimenter. Following a 15-20 minute acclimation period in the behavior chamber, the mechanical and thermal thresholds were tested as previously described (Marsh D, Dickenson A, Hatch D, Fitzgerald M. Epidural opioid analgesia in infant rats II: responses to carrageenan and capsaicin. Pain 1999; 82:33-38. doi:10.1016/50304-3959(99)00029-9; Walker S M, Meredith-Middleton J, Cooke-Yarborough C, Fitzgerald M. Neonatal inflammation and primary afferent terminal plasticity in the rat dorsal horn. Pain 2003; 105:185-195). Mechanical threshold is determined by application of an increasing series of calibrated Von Frey (VF) hairs to the medial side of the dorsal surface of the hindpaw, which is innervated by the saphenous nerve. After another 10-15 minute rest period, a water bath of varying temperatures is used to measure heat sensitivity. Mice were gently held and both hindpaws were submerged into the water. Time until a hindpaw flexion withdrawal response was detected was recorded as the latency. 20 seconds was set as a cut-off time. 40° C. and 45° C. were tested for P7 cohorts (1-7d post carrageenan) while 45° C. and 50° C. were tested for mice≥P14. This follows a similar strategy to that previously described by Marsh et al (Marsh D, Dickenson A, Hatch D, Fitzgerald M. Epidural opioid analgesia in infant rats II: responses to carrageenan and capsaicin. Pain 1999; 82:33-38. doi:10.1016/S0304-3959(99)00029-9.) and Walker et al (Walker S M, Meredith-Middleton J, Cooke-Yarborough C, Fitzgerald M. Neonatal inflammation and primary afferent terminal plasticity in the rat dorsal horn. Pain 2003; 105:185-195.) in which different maximal temperatures are required between these two ages. Both mechanical and thermal tests were performed 3 times at 5 minute intervals. The average of the three trials was determined per mouse, per time point/condition. The average values are reported as mean ±SEM after normalization to age-matched naives. For siRNA injected mice, DRG receptor expression (using PCR) is verified in the control or IGFr1 targeting groups to confirm validity of behavioral results obtained from these cohorts. In a few instances, individual mice did not achieve significant knockdown and are not included in the analysis.

Ex vivo preparation and intracellular recording for skin prep. The ex vivo hairy hindpaw skin/saphenous nerve/ dorsal root ganglion (DRG)/spinal cord (SC) somatosensory system recording preparation was performed as described previously (Jankowski M P, Lawson J J, McIlwrath S L, Rau K K, Anderson C E, Albers K M, Koerber H R. Sensitization of cutaneous nociceptors after nerve transection and regeneration: possible role of target-derived neurotrophic factor signaling. J. Neurosci. 2009; 29:1636-47. doi:10.1523/JNEUROSCI.3474-08.2009; Jankowski M P, Ross J L, Weber J D, Lee F B, Shank A T, Hudgins R C. Age-dependent sensitization of cutaneous nociceptors during developmental inflammation. Mol Pain 2014; 10:34. doi: 10.1186/1744-8069-10-34; Lawson J J, McIlwrath S L, Woodbury C J, Davis B M, Koerber H R. TRPV1 Unlike TRPV2 Is Restricted to a Subset of Mechanically Insensitive Cutaneous Nociceptors Responding to Heat. J. Pain 2008; 9:298-308. doi:10.1016/j jpain.2007.12.001; Ross J L, Queme L F, Shank A T, Hudgins R C, Jankowski M P. Sensitization of group III and IV muscle afferents in the mouse after ischemia and reperfusion injury. J. Pain 2014; 15:1257-70. doi:10.1016/j.jpain.2014.09.003). Briefly, mice are anesthetized with ketamine and xylazine (90 and 10 mg/kg, respectively) and intracardially perfused with oxygenated (95% $O_2$-5% $CO_2$) artificial cerebrospinal fluid (aCSF; in mM: 1.9 KCl, 1.2 $KH_2PO_4$, 1.3 $MgSO_4$, 2.4 $CaCl_2$, 26.0 $NaHCO_3$, and 10.0 D-glucose) containing 253.9 mM sucrose at a temperature of approximately 12° C. The spinal cord (caudal from ~T10) and the right hindlimb are excised and placed in a bath of this oxygenated aCSF. The hairy skin of the right hindpaw, saphenous nerve, L1-L5 DRGs and corresponding spinal cord segments were isolated in continuity and then transferred to a recording chamber containing chilled and oxygenated aCSF in which the sucrose was replaced with 127.0 mM NaCl. The skin is then pinned out on a stainless steel grid located at the bath/air interface to allow the dermal surface to be continuously perfused with the aCSF while the epidermis remained dry. The bath is finally warmed to 32° C. before recording.

Intracellular single unit recording is performed in sensory neuron somata contained within the L2 or L3 DRGs using quartz microelectrodes (impedance >150 MΩ) containing 5% Neurobiotin (Vector Laboratories, Burlingame, Calif.k) in 1 M potassium acetate. Sensory neuron somata in the L2/L3 DRGs with axons in the saphenous nerve are identified by electrical simulation to the side of the nerve through a suction electrode during intracellular recording. If a cell is found to be driven by this electrical stimulus, then the cutaneous receptive fields (RF) are localized with a soft brush and/or von Frey filaments. When cells are driven by the nerve but have no mechanical RF, a thermal search is conducted by applying hot (~53° C.) and/or cold (~1° C.) physiological saline to the skin.

Response characteristics of individual DRG cells are determined by first applying mechanical and then thermal stimuli to the hairy skin. For mechanical stimulation, RFs are probed for 1-2s with an increasing series of calibrated VF filaments ranging from 0.07 g to 10 g. When feasible, a mechanical stimulator that delivered a digitally controlled mechanical stimulus is employed, which consists of a tension/length controller (Aurora Scientific) attached to a probe with a 1 mm diameter aluminum tip. Computer controlled 5s square waves of 1, 5, 10, 25, 50 and 100 mN were applied to the cell's RF in these instances. In order to compare these results to those of the VF stimulation, units in mN are converted to grams based on the 1 mm probe diameter. After mechanical stimulation, a controlled thermal stimulus was applied using a 3×5 mm contact area peltier element (Yale Univ. Machine Shop) or saline stimuli as described. The controlled thermal stimulus consisted of a variable cold ramp that started at 32° C. and dropped to approximately 3-4° C., which was held for 2-3s and allowed to return slowly to the bath temperature (32° C.). Bath temperature is held for a few seconds (-2-3s) and then a heat ramp is initiated, which delivers an increasing heat stimulus to the RF up to 52° C. The ramp increases in temperature from 32° C. to 52° C. in 12s. The 52° C. stimulus is held for 5s and then the ramp returns the RF to 32° C. in 12s. Adequate recovery times (approx. 20-30s) are employed between all stimulations. The repetitive stimulation of the RFs with hot saline was not found to sensitize nociceptors during the recording experiments. No differences were found in recorded fibers from the beginning of an experiment to those obtained at the end.

When fibers were unable to be fully characterized by controlled mechanical and thermal stimulation but were partially characterized by one of the controlled stimuli and brush or saline stimuli, these cells were also included for determination of afferent subtype prevalence and for the properties in which Applicant obtained controlled data. All responses are recorded for offline analysis (Spike2 software, Cambridge Electronic Design). Conduction velocities of the recorded afferents were then calculated from spike latency and the distance between stimulating and recording electrodes (measured directly along the nerve). Firing rates were determined by calculating the peak firing after binning the responses in 200 ms bins.

Ex vivo recording for muscle prep: Dissection of the preparations have been described in detail previously in adults (Jankowski, M. P. et al. Sensitization of cutaneous nociceptors after nerve transection and regeneration: possible role of target-derived neurotrophic factor signaling. J Neurosci 29, 1636-1647 (2009) and in neonates (Jankowski M P, Ross J L, Weber J D, Lee F L, Shank A T, Hudgins R C. Age-dependent sensitization of cutaneous nociceptors during developmental inflammation. Mol. Pain. 10: 34. (2014)) and are performed as described. Electrophysiological recording and tissue collection are performed as described previously (Jankowski, M. P. et al. Sensitization of cutaneous nociceptors after nerve transection and regeneration: possible role of target-derived neurotrophic factor signaling. J Neurosci 29, 1636-1647 (2009); Jankowski M P, Ross J L, Weber J D, Lee F L, Shank A T, Hudgins R C. Age-dependent sensitization of cutaneous nociceptors during developmental inflammation. Mol. Pain. 10: 34. (2014); Ross J L, Queme L F, Shank A T, Hudgins R C, Jankowski M P. Sensitization of group III and IV muscle afferents after ischemia and reperfusion injury. J. Pain. 15, 1257-70. (2014).). The muscle preparation will use the hindpaw muscles and tibial nerve instead of the median and ulnar nerves described in that study (Ross J L, Queme L F, Shank A T, Hudgins R C, Jankowski MP. Sensitization of group III and IV muscle afferents after ischemia and reperfusion injury. J. Pain. 15, 1257-70. (2014)). Physiological properties measured are: 1) mechanical firing, thresholds and dynamic response properties at varied mechanical forces; 2) thermal thresholds, firing rates and mean peak instantaneous frequencies during a heating/cooling stimulus; 3) chemical responsiveness to different combinations of lactate, ATP and pH (Light, A. R. et al. Dorsal root ganglion neurons innervating skeletal muscle respond to physiological combinations of protons, ATP, and lactate mediated by ASIC, P2X, and TRPV1. J Neurophysiol 100, 1184-1201 (2008); Light A. R. et al. Gene expression alterations at baseline and following moderate exercise in patients with chronic fatigue syndrome and fibromyalgia syndrome. J Intern Med. 271, 64-81 (2012); Ross J L, Queme L F, Shank A T, Hudgins R C, Jankowski M P. Sensitization of group III and IV muscle afferents in the mouse after ischemia and reperfusion injury. J. Pain 2014; 15:1257-70. doi:10.1016/j.jpain.2014.09.003.) (for muscle preparations only); 4) conduction velocity (CV); 5) somal spike shape (i.e. broad or narrow spike, inflected or uninflected spike, AP and AHP duration); 6) presence or absence of spontaneous activity. Afferents will be grouped based upon response characteristics, conduction velocities (CV) and spike shapes.

Cells are intracellularly recorded and physiologically characterized from the various groups in which at least 20 cells were obtained from a minimum of 3 mice per condition.

Primary DRG cultures and single cell cDNA amplification. For primary DRG neuron cultures, Applicant followed described procedures (Jankowski M P, Cornuet P K, McIlwrath S, Koerber H R, Albers K M. SRY-box containing gene 11 (Sox11) transcription factor is required for neuron survival and neurite growth. Neuroscience 2006; 143:501-514; Malin S A, Davis B M, Molliver D C. Production of dissociated sensory neuron cultures and considerations for their use in studying neuronal function and plasticity. Nat. Protoc. 2007; 2:152-60. doi:10.1038/nprot.2006.461) but used DRGs from P14 male mice. Animals were first anesthetized and intracardially perfused with Hank's Balanced Salt Solution (HBSS). DRGs (all spinal levels) are then dissected and collected in HBSS and dissociated using cysteine/papain (0.03%, Sigma, and 20 U/mL, Worthington) followed by collagenase II (0.3%, Worthington), and then triturated with fire-polished glass pipettes in F12 complete media (F12 containing 10% fetal bovine serum and 1% penicillin/streptomycin) before plating onto poly-d-lysine/laminin (20 µg/mL each, Sigma) coated glass coverslips (Menzel, Germany) that is placed in 35 mm petri dishes. Cells are allowed to incubate at 37° C./5% $CO_2$ for 1-2 hours and then flooded with F12 complete media alone (untreated) or media containing 50 ng/mL GH (Genscript). Cells are then allowed to incubate at 37° C./5% $CO_2$ for 24 hrs. At this time, media is removed and cells were flooded with single cell PCR buffer (In mM: 140 NaCl, 10 glucose, 5 KCl, 10 HEPES, 1 $MgCl_2$, and 2 $CaCl_2$). Then individual neurons (n=20) that were qualitatively determined to be in the medium to small diameter range were collected using borosilicate electrodes and Cell Tram Vario system (Eppendorf) under bright field optics using a Leica inverted microscope. Images of the various cell culture conditions were obtained using modified differential interference contrast on a Leica inverted fluorescence microscope.

All collected single cells are used in realtime PCR reactions based on a modified protocol from Kurimoto et al (Kurimoto K, Yabuta Y, Ohinata Y, Ono Y, Uno K D, Yamada R G, Ueda H R, Saitou M. An improved single-cell cDNA amplification method for efficient high-density oligonucleotide microarray analysis. Nucleic Acids Res. 2006; 34:e42. doi:10.1093/nar/gkl050.) and Ross et al (Ross J L, Queme L Q, Cohen E R, Green K J, Lu P, Shank A T, An S, Hudgins R C and J M. Muscle IL1β drives ischemic myalgia via ASIC3-mediated sensory neuron sensitization. J Neurosci. 2016; 36: 6857-6871). Single cells were first expelled from the borosilicate electrodes into individual tubes containing lysis buffer from the Message Booster cDNA Synthesis Kit (Epicentre/Illumina) and prokaryotic spike RNAs (1000 copies of LYS transcripts) are used for internal and reverse transcription controls since internal controls such as GAPDH will consistently vary from single cell to cell. Single cell RNAs were reverse transcribed with Superscript III (Invitrogen) primed by an Oligo (dT) containing a T7 RNA polymerase promoter. cDNAs then undergoes in vitro transcription, RNA is purified, and new cDNAs are produced using Superscript III. cDNAs are then diluted and ran in duplicate in standard SYBR Green realtime PCR reactions (20 ng/reaction) on a Step-One realtime PCR machine (Applied Biosystems). The forward and reverse primer sequences for GAPDH and LYS are as follows: GAPDH: forward: 5'-ATGTGTCCGTCGTGGATCTGA-3'(SEQ ID NO:6); reverse: 5'-ATG CCT GCT TCA CCA CCT TCT T -3' (SEQ ID NO:7); LYS: forward: 5'-GCC ATA TCG GCT CGC AAA TC-3'(SEQ ID NO:8); reverse: 5'-AAC GAA TGC CGA AAC CTC CTC-3'(SEQ ID NO:9). GAPDH was first tested in each sample to verify acquisition of single cell cDNAs. However, cycle time (Ct) values for all targets in single cell PCR reactions were normalized to the LYS spike RNA controls.

Whole DRG or skin RNA isolation, reverse transcription and realtime PCR. Animals were first anesthetized as described above. The mice are then intracardially perfused with ice cold 0.9% NaCl prior to dissection of skin or DRGs. RNA isolation from the hairy skin is performed using Trizol (Thermo) followed by RNA cleanup with the Qiagen RNeasy Mini Kits while L2 and L3 DRG RNA is isolated using Qiagen RNeasy mini kits for animal tissues using the supplied protocol (n=3-5 per condition and time point). RNA concentrations are then determined by obtaining A260 readings on a Nanodrop spectrometer (Thermo). Purified RNA is treated with DNase I (Invitrogen) and then DNased RNA is reverse transcribed using Superscript II Reverse Transcriptase (Invitrogen). For realtime PCR, 25 ng samples of cDNA are added to a SYBR Green Master Mix (Applied Biosystems) containing the appropriate primer combinations and run in duplicate on an Applied Biosystems Step-ONE realtime PCR machine. Forward and reverse primer sequences used in realtime PCR reactions for IL1β, GDNF, NGF, IGFr1, and GAPDH can be obtained from Ross et al (Ross J L, Queme L F, Shank A T, Hudgins R C, Jankowski M P. Sensitization of group III and IV muscle afferents in the mouse after ischemia and reperfusion injury. J. Pain 2014; 15:1257-70. doi:10.1016/j.jpain.2014.09.003.), Jankowski et al (Jankowski M P, Lawson J J, McIlwrath S L, Rau K K, Anderson C E, Albers K M, Koerber H R. Sensitization of cutaneous nociceptors after nerve transection and regeneration: possible role of target-derived neurotrophic factor signaling. J. Neurosci. 2009; 29:1636-47. doi:10.1523/JNEUROSCI.3474-08.2009) or Elitt et al (Elitt C M, McIlwrath S L, Lawson J J, Malin S a, Molliver D C, Comuet P K, Koerber H R, Davis B M, Albers K M. Artemin overexpression in skin enhances expression of TRPV1 and TRPA1 in cutaneous sensory neurons and leads to behavioral sensitivity to heat and cold. J. Neurosci. 2006; 26:8578-8587). Primer sequences for the GH receptor are as follows: Forward: 5'-GCC TCT ACA CCG ATG AGT AA-3' (SEQ ID NO:10); Reverse: 5'-GGA AAG GAC TAC ACC ACC T-3'(SEQ ID NO:11). Primer sequences for TNFa are: Forward: 5'-TCGGAAAGAAATGTCCCAGGTGGA-3' (SEQ ID NO:12); Reverse: 5'-TGGAACTGGTTCTCCT-TACAGCCA -3' (SEQ ID NO:13) and sequences for IL6 are: Forward: 5'-ACTGATGCTGGTGACAAC-3'(SEQ ID NO:14); Reverse: 5'-CCGACTTGTGAAGTGGTATAG-3' (SEQ ID NO:15). Cycle time (Ct) values are normalized to GAPDH and changes in expression are calculated as a ΔΔCt value that is determined by subtracting the Ct values of the gene of interest from the GAPDH (or LYS) internal control for each sample and compared among samples. Fold change is described as $2^{\Delta\Delta Ct}$ (Applied Biosystems) and 2-fold change equals 100% change (mean±SEM).

Protein isolation and western blotting. Similar to RNA isolation, animals are first anesthetized as described above and intracardially perfused with ice cold 0.9% NaCl. Skin or muscle samples or L2/L3 (cutaneous related injuries) or L3/L4/L5 (muscle related injuries) DRGs pooled from two mice as indicated are then collected and homogenized in lysis buffer containing 1% sodium dodecyl sulfate (SDS), 10 mM Tris.HCl (pH 7.4), and protease inhibitors (1 µg/ml pepstatin,1 µg/ml leupeptin, 1 µg/ml aprotinin, 1 mM sodium orthovanadate and 100 µg/ml phenylmethylsulfonyl fluoride; Sigma Biochemicals). Then 20 µg samples from each condition are centrifuged and boiled 10 min in a denaturing buffer containing β-mercaptoethanol and SDS prior to gel electrophoresis. Samples are then separated on a 7.5-16% polyacrylamide SDS-PAGE gel and transferred to a PVDF (Millipore) membrane that is blocked in specialized LiCor blocking buffer. Membranes are then incubated in primary antibodies overnight at 4° C. (GAPDH: 1:2000, ProSci Inc; GH: 1:2000, GenScript; IGF-1: 1:1000, Abcam; IGFr1: 1:750, Acris). Antibody binding is visualized using 680 nm or 800 nm infrared dye-conjugated donkey anti-rabbit or donkey anti-chicken secondary antibodies (1:20, 000; LiCor) with detection using the LiCor Odyssey Imaging System (LiCor). Settings for detection were consistent between runs. Immunoreactive bands are analyzed by densitometry and quantified using NIH image J (RRID: nif-0000-30467) software. Band intensity is normalized to GAPDH and reported as a percent change (mean±SEM). A negative control and a peptide block control are also performed for the GH antibody. In this latter case, an equal dilution of the manufacturer's supplied peptide is incubated with the GH antibody (above) during blot processing. For the negative control, no primary antibody is used. Both controls followed the above procedures.

Data analysis. All data are presented as mean ±SEM. Behavioral assays were compared using one- or two-way repeated measures (RM) or standard analysis of variance (ANOVAs) with Holm Sidak or Tukey's post hoc tests. Peak firing rates (FR), mean peak instantaneous frequencies (IF) and thresholds to mechanical or heat stimuli are compared via one-way ANOVA with Holm Sidak post hoc as appropriate or Kruskal-Wallis one-way ANOVA on ranks with Dunn's post-hoc tests. Percent change in protein expression detected from Western blotting and gene expression changes in single cells or whole tissues are analyzed via one-way ANOVA with Tukey's post-hoc. Critical significance level was defined at $p<0.05$. Rare instances of statistical outliers defined as values greater than two standard deviations away from the mean are not included in the analysis.

Results

Cutaneous inflammation produces a localized reduction in GH levels. In order to first determine if cutaneous inflammation altered the levels of growth hormone (GH) in the injured skin of neonates, Applicant quantified GH protein in the hairy hindpaw skin using western blot analysis on mice with inflammation induced at P14. Applicant found that neonatal cutaneous inflammation (n=3-4 each) significantly decreased the levels of GH protein present in this target tissue one day after carrageenan injection initiated at P14. Hairy skin GH levels returned to that of naïve mice three days after cutaneous inflammation (FIG. 1, Panel A, Panel B).

Figure 7:
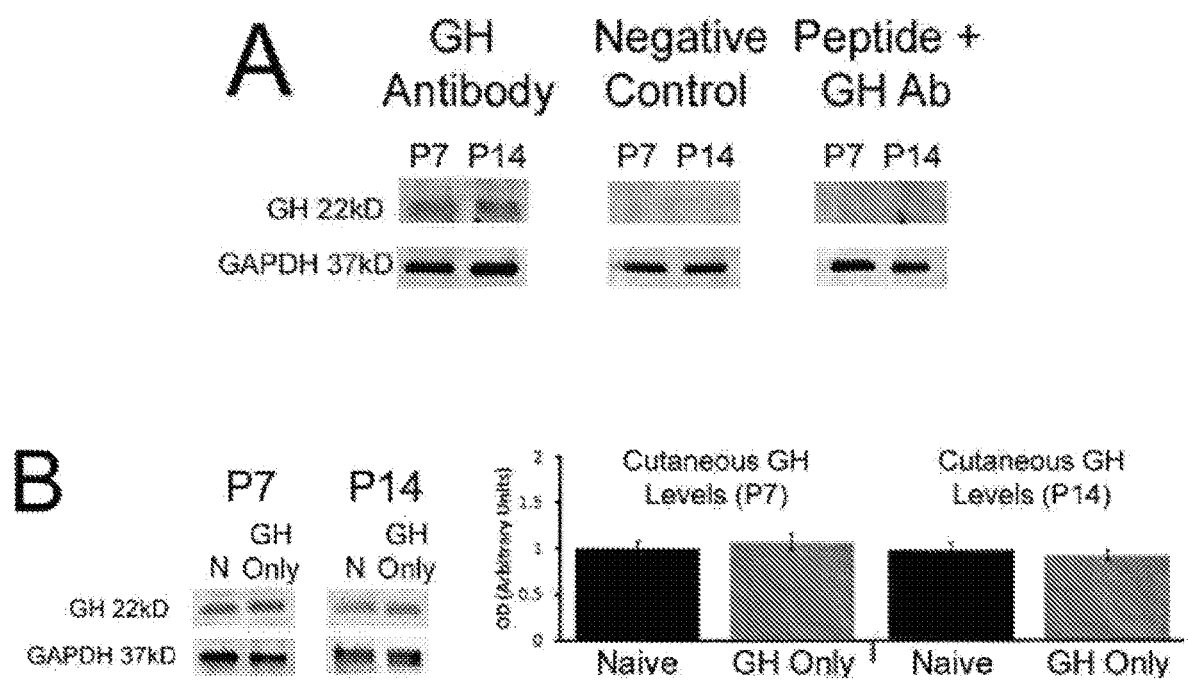
FIG. 7. Antibody controls for use of growth hormone (GH) antibody in western blotting and effects of GH treatment on cutaneous GH levels in naïve neonates. Panel A: In normal skin at P7 or P14, GH protein is detected at the predicted weight around 22 kD using a GH antibody. Negative control experiments show that without primary antibody incubation, no bands are detected for GH at 22 kD while GAPDH protein is readily detected in these samples. Processing blots with both the GH antibody and a GH blocking peptide also eliminates band detection at 22 kD while GAPDH is still detected. Panel B: Treating naïve neonates with GH for three days prior to analysis at 24 hrs after the final dose, does not significantly alter the levels of cutaneous GH detected in either P7 or P14 mice. One-way ANOVA with Tukey's post hoc test.

Applicant then delivered a three-day pretreatment of GH (0.5 mg/kg; 1x/d for 3d) and found that this was sufficient to prevent the reduction in hairy skin GH levels following carrageenan injection at P14 (FIG. 1, Panel A; $p>0.05$). Next, Applicant wanted to determine if the observed GH reduction in hairy skin was specific to the inflamed target tissue or was a broad effect of peripheral inflammation. Similar western blot analyses were performed on forepaw and back skin from mice that received carrageenan injection into the hairy hindpaw skin and found that no statistically significant differences in GH levels were detected (FIG. 1, Panel B; $p>0.05$). Both negative and peptide block controls verified GH antibody specificity for western blotting. GH injections into naïve neonates using this regimen were not found to increase cutaneous levels of GH (FIG. 7). These data suggest that cutaneous inflammation produces a transient GH reduction in the affected skin and a short, low dose GH pre-treatment reverses the inflammation induced GH decrease in the skin.

Exogenous GH treatment blocks injury induced mechanical and thermal hypersensitivity. As Applicant's data suggested that GH levels in the inflamed hairy skin of neonatal mice could be manipulated and restored, the effectiveness of an exogenous GH treatment was tested on the reported mechanical and thermal hypersensitivity during cutaneous inflammation at P7 or P14. Applicant first performed a dose response analysis based on the above information and previously reported data (Farris G M, Miller G K, Wollenberg G K, Molon-Noblot S, Chan C, Prahalada S. Recombinant rat and mouse growth hormones: risk assessment of carcinogenic potential in 2-year bioassays in rats and mice. Toxicol. Sci. 2007; 97:548-61. doi:10.1093/toxsci/kfm059). Mice were thus treated with one of three different doses of GH (0.1-0.5 mg/kg, ip.) once a day beginning three days prior to injury up through the day of inflammation, or another cohort of mice was given a single injection of GH (at 0.5 mg/kg, ip.) at the same time as cutaneous inflammation. Applicant found that inflammation-induced mechanical and heat hypersensitivity one day after injury was blocked by varying doses of the three-day pre-treatment strategy regardless of the age of initial insult. A single injection of GH at the highest dose used; however, was insufficient to block carrageenan induced hyper-responsiveness to mechanical and thermal stimuli at P14 while a single dose of GH partially blunted heat but not mechanical hypersensitivity at P7. (FIG. 8).

Figure 2:
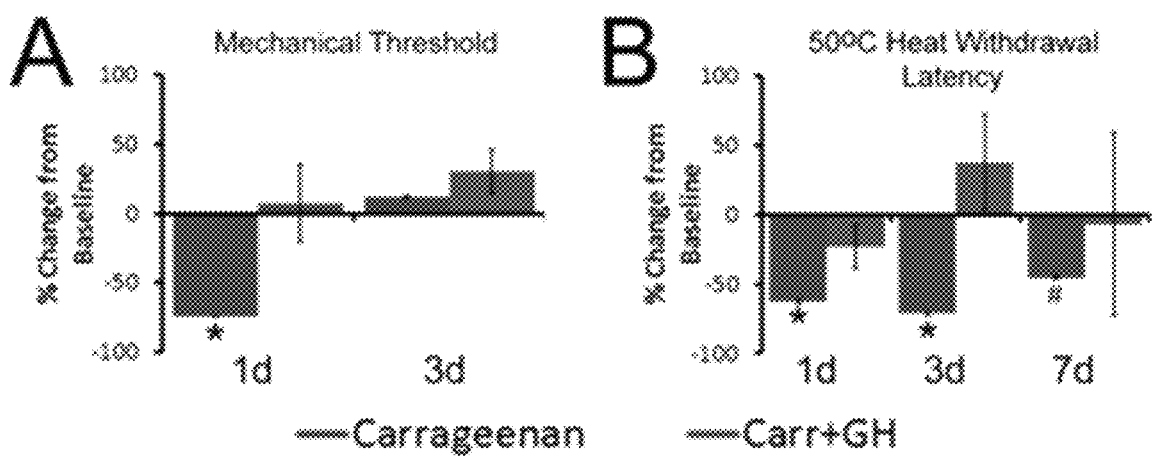
FIG. 2: Effects of GH pretreatment on peripheral hypersensitivity after P14 carrageenan injection. Panel A: Mechanical hypersensitivity during P14 inflammation (measured as a percent change in thresholds relative to baseline) was blocked by GH pretreatment at ld. No differences were found between mice injected with carrageenan alone or those treated with carrageenan plus GH at 3d; however, both of these groups differed from mice that received carrageenan only at the ld time point. Panel B: Hairy skin inflammation also reduced the heat withdrawal latencies to 50 oC water at ld and 3d post carrageenan, but this was completely blocked by GH pretreatment at all time points tested. By 7d, a partial restoration of heat hypersensitivity was found in mice with carrageenan injection only; however, these mice were not different than those treated with GH at this 7d time point. GH treated mice with hairy hindpaw skin inflammation did not change relative to their baseline levels at any time point post inflammation. * $p<0.05$ vs. baseline and GH treated mice, # $p<0.05$ vs. baseline, but not time matched GH treated mice; 2-way RM ANOVA/Holm Sidak.
Figure 8:
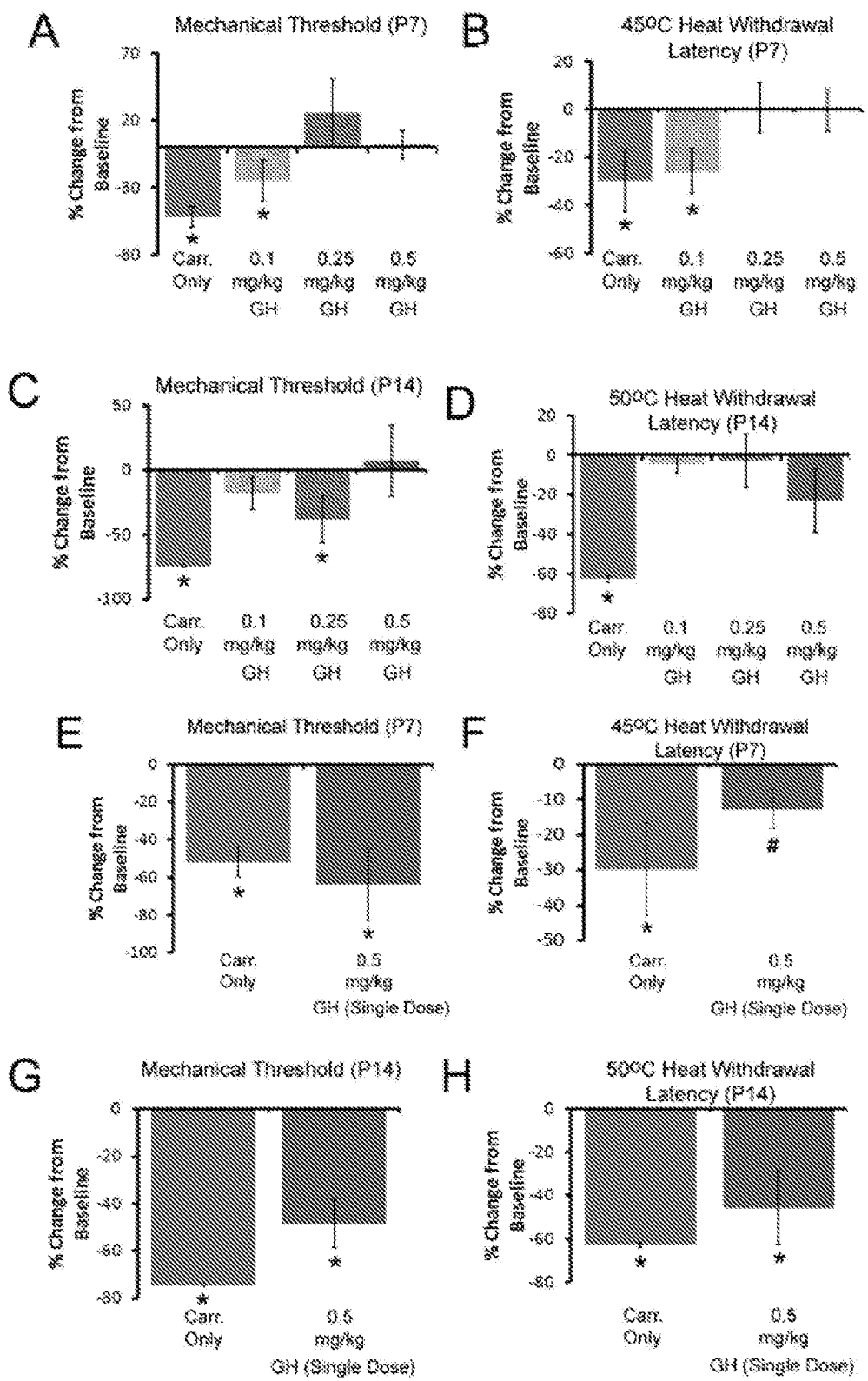
FIG. 8. Dose response analysis of the effectiveness of growth hormone (GH) treatment on mechanical and thermal sensitivity 1 d post inflammation at P7 or P14.Three different doses of GH (0.1, 0.25 and 0.5 mg/kg) were injected (ip.) 1× per day for 3d prior to carrageenan induced hairy hindpaw skin inflammation at P7 or P14. Alternatively, a single injection of the highest dose (0.5 mg/kg) was given at the same time as peripheral inflammation in other cohorts. With regards to the 3d pretreatment strategy, mechanical hypersensitivity (Panel A) observed during inflammation is blocked at the higher doses of GH, as was heat hypersensitivity (Panel B). Similar results were also found in mice at P14 for both mechanical and heat hypersensitivity (Panel C, Panel D). A single dose of 0.5 mg/kg GH delivered at the time of inflammation however was insufficient to fully block mechanical (8E) hypersensitivity found during carrageenan induced inflammation at P7. The single dose of GH at P7 was sufficient however to partially reduce heat hypersensitivity at P7 (Panel F). No effects of single dose GH were found. Similar results were found with a single dose of GH in mice inflamed/treated at P14 in regard to the observed mechanical (Panel G) or heat, (Panel H) hypersensitivity. *$p<0.05$ vs.baseline; #$p<0.05$ vs. baseline and carrageenan alone; One-way ANOVA/Holm Sidak post hoc.

Applicant therefore assessed the time course of GH effects on neonatal inflammatory hypersensitivity using the dosing regimen that was effective in all behavioral tests (0.5 mg/kg, ip.; 1x/d for 3d prior to inflammation; see FIG. 8. Specifically, mechanical thresholds in the ipsilateral hindpaw one day (1d) after carrageenan injection (at P14) were significantly decreased compared to baseline, but this returned to normal levels by three days (3d; FIG. 2, Panel A; n=12, $p<0.05$). However, GH pre-treatment completely blocked this decrease at 1d and showed no differences versus baseline at 3d (FIG. 2, Panel A; n=9, $p<0.05$). A seven day (7d) time point was not analyzed due to the difficulty of mechanical testing on the hairy skin in older mice (P21). No changes were found in the contralateral limbs in any group at 1d (not shown).

Heat withdrawal latencies to 50° C. water were significantly decreased 1d and 3d ($p<0.05$) after P14 carrageenan injection compared with baseline. Heat hypersensitivity returned towards uninjured levels by 7d post inflammation, but did not fully recover to naïve levels. GH pretreatment, however, completely inhibited the carrageenan induced reduction in heat withdrawal latency at all time points (FIG. 2, Panel B). No differences were detected between any group during a 45° C. heat stimulus ($p>0.05$, not shown). GH pretreatment at P14 had no effect on baseline mechanical sensitivity (i.e. without injury) or heat withdrawal times compared to untreated naives (see FIG. 9). These data suggest that an exogenous GH treatment can block mechanical and thermal hypersensitivity if given before neonatal cutaneous inflammation.

Exogenous GH pretreatment blocks cutaneous afferent sensitization during neonatal peripheral inflammation. To then determine the effects of GH pretreatment on the response properties of primary sensory neurons, Applicant performed single unit recordings with Applicant's neonatal ex vivo hairy hindpaw skin/saphenous nerve/DRG/spinal cord recording preparation, at 1d and 3d post inflammation. Two categories of sensory afferents are detected based on conduction velocity (CV) during development due to ongoing myelination. "A"-fibers were defined as those that conduct at least twice as fast as the other sensory neurons ("C"-fibers) in a given experiment. Based on these criteria, some fibers could be classified as "A"-fibers if they conducted at the higher end of the adult C-fiber range for rodents (1.2 m/s). However, it should be noted that only 13 cells out of 738 recorded in Applicant's study fell into this category (i.e. were classified as "A"-fibers despite conducting slower than 1.2 m/s). Furthermore, this categorization is consistent with previous reports analyzing response properties of neonatal sensory neurons. At P14, the average CVs for A-fibers were 5.14 m/s, and the average CVs for C-fibers were 0.56 m/s. No differences in A- or C-fiber CVs were found between any of the groups.

Applicant detected no differences after carrageenan injection in the rapidly or slowly adapting low threshold mechanoreceptors (faster conducting cells with narrow spikes), nor were there any differences detected in the low threshold mechanically sensitive and cold sensitive C-fibers (CMC;

slower conducting cells with narrow spikes). There were also no differences in the mechanically insensitive but cold (CC) or heat (CH) sensitive C-fiber neurons (slower conducting, broad spiking) among any of Applicant's experimental groups (not shown). Therefore, the remainder of the study focused on the myelinated nociceptors (faster conducting, broad spiking afferents) that were mechanically sensitive, and sometimes thermally sensitive ("A"-high threshold mechanoreceptors (A-HTMRs): AM or A-polymodal (APM)), or the unmyelinated nociceptors (slower conducting, broad spiking fibers) with these types of responses ("C"-HTMR: CM or CPM).

Figure 3:
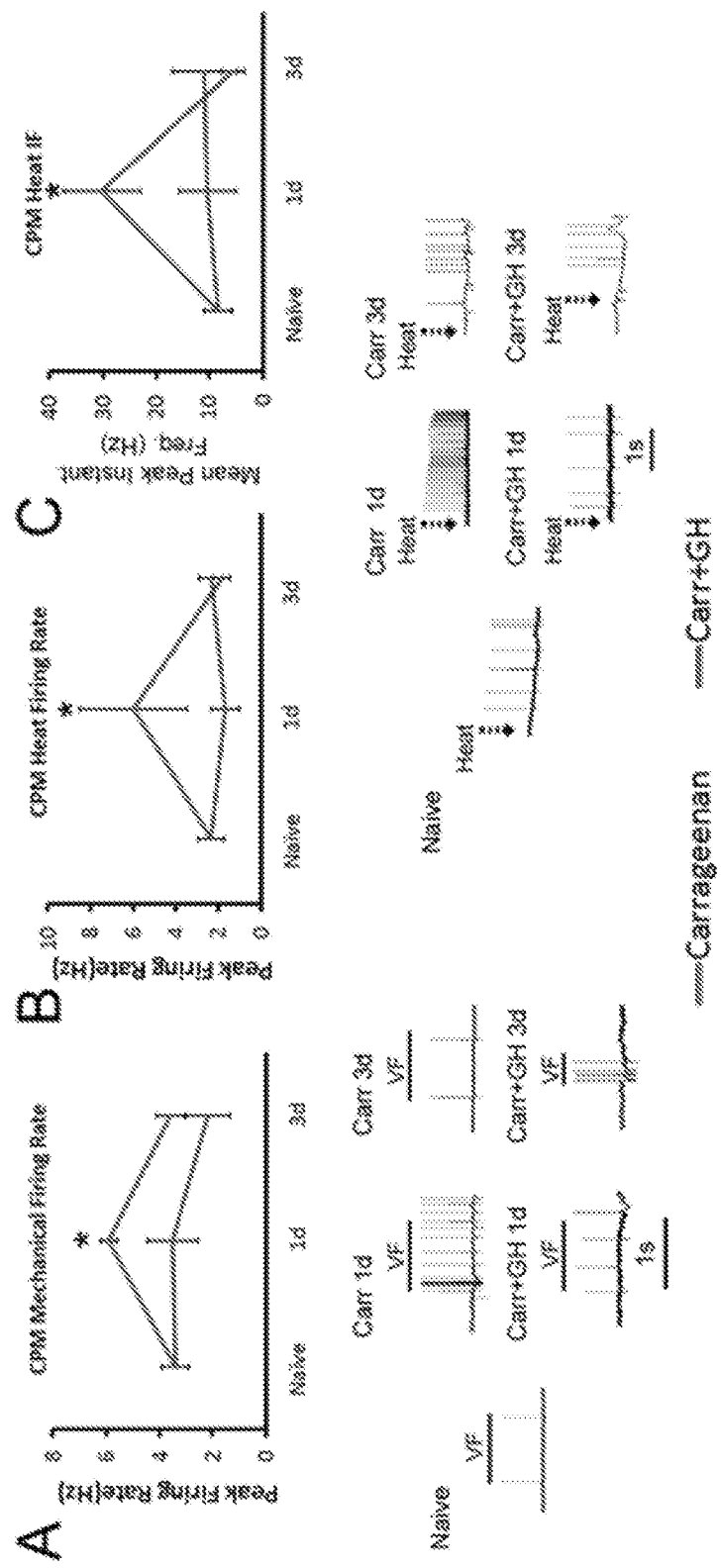
FIG. 3: Growth hormone (GH) pretreatment blocks hypersensitivity of "C"-fiber sensory neurons to mechanical and thermal stimuli during cutaneous inflammation initiated at P14. At P14, carrageenan was found to increase the firing of slowly conducting (C-fiber) polymodal nociceptors (CPM) to both mechanical (Panel A) and heat (Panel B, Panel C) stimuli. GH pretreatment in mice with hairy skin inflammation however, blocked all of the observed changes in CPM neurons at P14. Mechanical and heat hyper-responsiveness in CPM neurons resolved by 3d post inflammation while GH treated mice with inflammation showed no variations in CPM neuron responses to these stimuli at any time point relative to uninjured control cells. Examples of corresponding responses to various stimuli are presented with each panel(s). VF=von Frey filament (peak response for cell). *$p<0.05$ vs. naïve; # $p<0.05$ vs. 1d inflammation; One-way ANOVA on Ranks/Dunn's post hoc.

Consistent with Applicant's previous findings at P14, CPM mechanical firing rates (FRs), heat FRs and heat peak instantaneous frequencies (IFs) were all increased (n=7 (mechanical) and n=5 (heat)) 1d after carrageenan induced inflammation (p<0.05) compared with naïves (n=10 and n=7, respectively; p<0.05). These alterations in C-fiber response properties were all blocked by GH pretreatment (n=4 for both mechanical and heat responsive cells; p>0.05; FIG. 3, Panel A-, Panel C). No differences in mechanical or heat firing in CPMs were found between groups at 3d post inflammation (FIG. 3; Inflammation Only: n=17 (mechanical) and n=11 (heat); Inflammation+GH: n=6 (for both mechanical and heat responsive cells)). Meanwhile, the CM mechanical FRs and thresholds had no statistical changes at any time point between any groups (n=4-9; not shown). A-fiber HTMR mechanical FRs were not found to be different post-carrageenan (n=10) compared to naïves (n=13; p>0.05; not shown). Heat FRs were also unaffected in the A-HTMR neurons at 1d (n=3-6; not shown). These data suggest that P14 cutaneous inflammation sensitizes CPM nociceptors, but not A-fiber HTMRs; however, this can be blocked by GH pretreatment.

Figure 4:
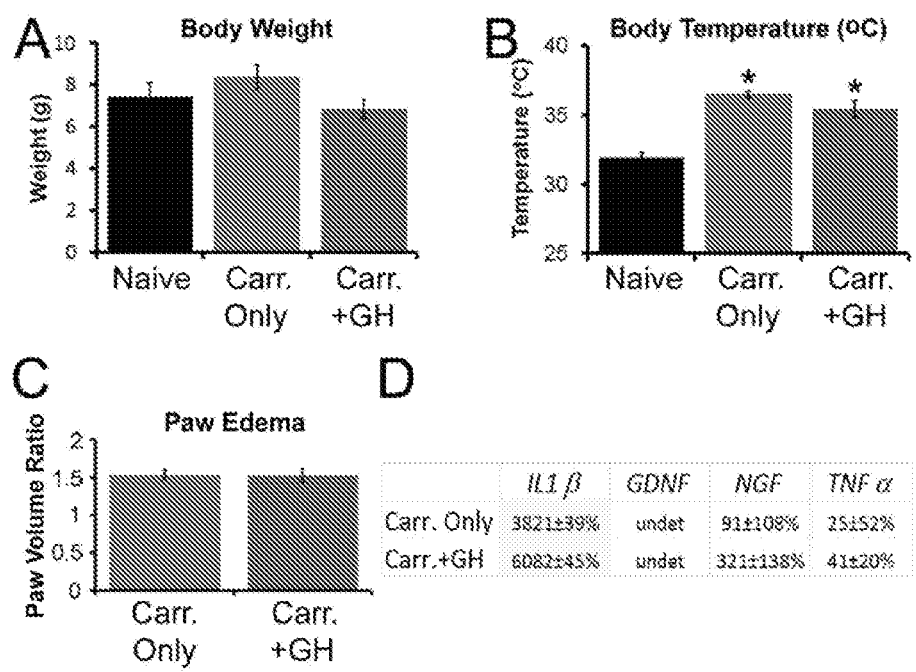
FIG. 4: Analysis of body weight, temperature, paw edema and mRNA expression of select cytokines and growth factors in skin after GH pretreatment in mice after P14 inflammation. At P14, no differences in body weight were observed in any of the three groups (Panel A) however, carrageenan injection induced an increase in body temperature that was similarly observed in the GH treatment group (Panel B). * $p<0.05$ vs. naive; #$p<0.05$ vs. naïve, but not Carr.+GH treated mice; n=4-11/group; One-way ANOVA/Holm Sidak post hoc. Carrageenan induced paw edema was not affected by a GH pretreatment regimen (Panel C). Only IL1β was upregulated in the hairy hindpaw skin of P14 inflamed neonates (Panel D). GH treated neonates with cutaneous inflammation also showed upregulation of this cytokine in the skin. Although both groups showed significant upregulation of IL1β in the skin after inflammation, there were no statistically significant differences between these groups in regard to relative gene expression. Greyed out values indicate $p<0.05$ vs. naïve only; n=3-7 for Panel C, Panel D. undet=undetectable. One-way ANOVA/Tukey's post hoc. Values are presented as a percent change from naïve.

A short course of low dose GH in inflamed mice does not induce classic side effects of extended GH therapy or alter cutaneous inflammatory responses to carrageenan. Applicant next determined if transient, low dose GH therapy produced any of the known side effects of prolonged GH therapy in Applicant's mouse model of cutaneous inflammation such as altered body weight, temperature or induction of hyperglycemia. Applicant found that the highest dose (0.5 mg/kg ip.; 1x/d for 3d prior to inflammation) used to effectively block mechanical and thermal responsiveness in inflamed mice was not sufficient to significantly alter body weight at P14 (FIG. 4, Panel A; n=4-14; p>0.05), nor did it produce detectable ketones in the urine (indirect measure of insulin resistance; not shown). While a significant increase in body temperature in mice that were injected with carrageenan compared to uninjured naives was detected, this was not further affected by the injection of GH (FIG. 4, Panel B; p<0.05).

As Applicant's results suggested robust effects of GH pretreatment on neonatal hypersensitivity to cutaneous inflammation, Applicant wanted to determine if these effects were due to alterations in the peripheral inflammatory response. Applicant thus measured paw edema and also performed realtime PCR on the hairy hindpaw skin for various cytokines and growth factors in cohorts. Applicant found that GH treatment did not alter carrageenan induced paw edema (FIG. 4, Panel C; p>0.8), and had no effects on the induction of cutaneous cytokines and growth factors after P14 inflammation (FIG. 4, Panel D). Of the numerous factors that were screened in this study, only the inflammatory cytokine interleukin 1β (IL1β) was found to be significantly upregulated in the skin after carrageenan injection into the hairy hindpaw skin at P14, but GH pretreatment did not prevent its upregulation. No increases in nerve growth factor (NGF) or tumor necrosis factor a (TNFa) mRNA were found in the skin after P14 inflammation (FIG. 4, Panel D). Significant levels of glial cell line-derived neurotrophic factor (GDNF) or IL6 mRNA in any group using these reaction conditions and primer sets (not shown) were not detected. Thus GH does not appear to induce classic side effects of extended GH therapy, and the GH effects on peripheral hypersensitivity during neonatal inflammation are unlikely to reflect a suppression of the inflammatory response within the skin.

Figure 10:
FIG. 10. Effects of GH pre-treatment on cutaneous GH levels and behavioral responsiveness in P7 neonates with hairy hindpaw skin inflammation. Panel A: Relative to naïve skin, the levels of GH protein detected in the hairy hindpaw skin is reduced 36.5% (±10%) 1d after cutaneous inflammation at P7. Levels return to that detected in naïve mice by 3d. GH pretreatment in inflamed P7 neonates completely blocked the reduction in GH levels induced by inflammation at 1d. No differences in GH protein were detected in mice with GH pretreatment and cutaneous inflammation at 3d relative to naïves. These levels were similar to that observed at the 1d time point in GH treated mice with P7 inflammation. Panel B: Analysis of the forepaw (FP) or back skin of naïve mice or skin from these same areas obtained from mice with hairy hindpaw skin inflammation revealed no differences in GH protein levels. Panel C: P7 neonates with cutaneous inflammation show significantly reduced mechanical withdrawal thresholds relative to their baseline at 1d and this is restored by 3d. GH pretreatment completely blocked mechanical hypersensitivity induced by carrageenan injection at 1d and this was also maintained throughout testing at 3d and 7d post injury in these cohorts. Panel D: Heat withdrawal latencies to 45° C. water are reduced by P7 inflammation at 1d and 3d and this returns to baseline by 7d post injury. GH pretreatment completely blocked this effect of carrageenan on heat responsiveness at all time points tested. GH treated mice with hairy skin inflammation did not vary from their baseline values for mechanical or heat sensitivity at any time point. *p<0.05 vs. naïve or baseline. One-way ANOVA with Tukey's or Holm Sidak post hoc tests.
Figure 10:
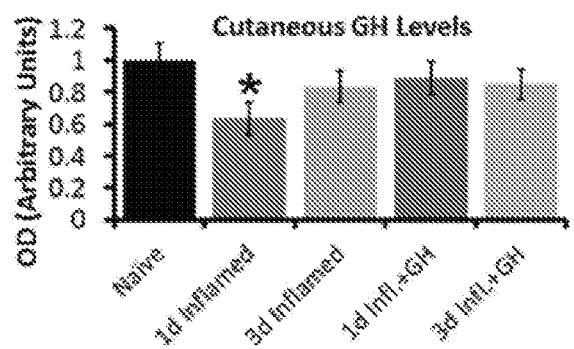
Figure 10:
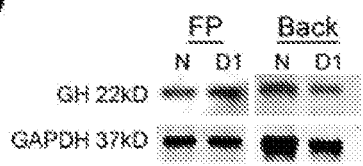
Figure 10:
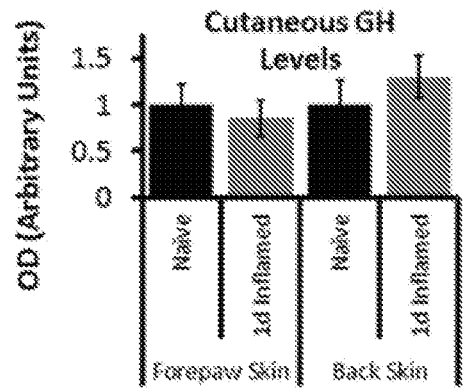
Figure 10:
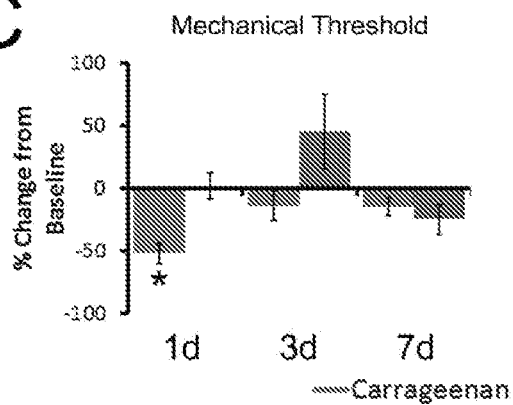
Figure 10:
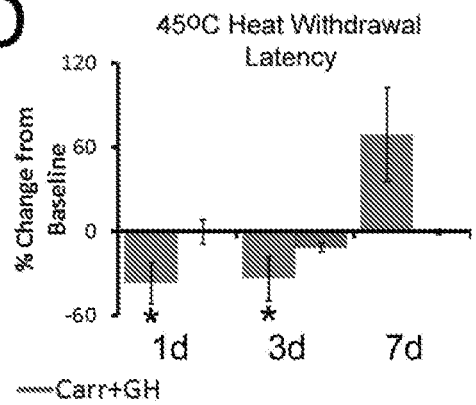

GH pretreatment regulates mechanical and thermal hypersensitivity after cutaneous inflammation at P7. Since data showed a profound effect of GH on neonatal hypersensitivity to inflammation at P14, Applicant wanted to assess whether similar results could be obtained in younger mice (P7). Overall, Applicant found highly similar effects of GH on carrageenan induced hypersensitivity when injury was sustained at P7. Applicant found that GH was also reduced specifically in the hairy skin after inflammation at P7 (FIG. 10, Panel A), B; n=3-4), which could be prevented with a GH pretreatment (p>0.05). In addition, the mechanical and heat hypersensitivity (at 45° C.) that was observed in these younger mice was also blocked with exogenous GH pretreatment. (FIG. 10, Panel C, D; n=11-13, p<0.05). Similar results on heat hypersensitivity were also detected at lower temperatures analyzed. Although carrageenan injection significantly decreased withdrawal latencies in response to a 40° C. heat stimulus at 1d compared to baseline (-21.7%±9.9%; p<0.05), no differences in heat withdrawal latency were detected in the GH treated group (-3.2%±10.2%; p>0.05). No differences were found among any of the groups at the 3d or 7d time points at this temperature however (not shown). Finally, no changes were found in the contralateral limbs in any group after P7 inflammation (not shown).

Figure 9:
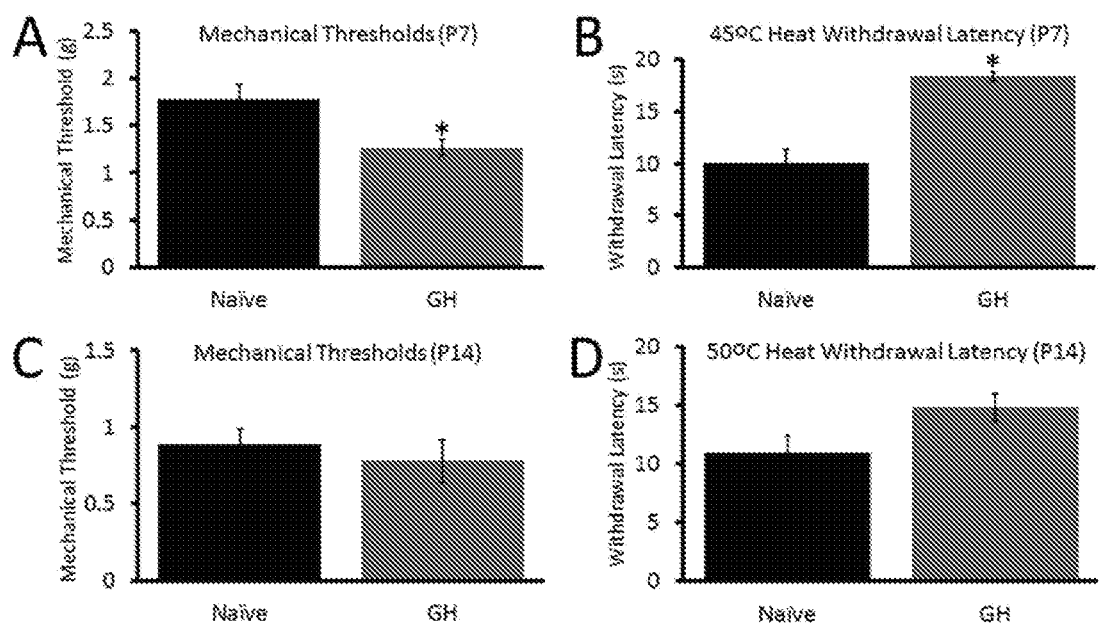
FIG. 9. Comparison of the effects of GH treatment on baseline mechanical and heat responsiveness in neonates at P7 or P14. GH treatment in un-inflamed mice at P7 reduces the baseline paw withdrawal threshold (in grams (g)) to mechanical stimulation of the hairy hindpaw skin compared to untreated naïve mice (Panel A). Heat withdrawal latencies (in seconds (s)) were also increased by GH at this neonatal age when specifically assessing 45° C. withdrawal latencies (Panel B). GH treatment however in P14 mice did not alter baseline mechanical thresholds (Panel C) or heat withdrawal latencies to 50° C. water (Panel D). *p<0.05 vs. naïve; ANOVA/Holm-Sidak post hoc.

Interestingly, when comparing raw baseline values between the groups, the mechanical withdrawal thresholds for both ipsilateral and contralateral hindpaws were decreased in the GH treated group compared to the baseline thresholds in untreated/naive neonates at P7 (see FIG. 9; p<0.05; not shown). In the absence of injury, GH pretreatment also appeared to increase the baseline withdrawal time to 45° C. heat compared to baseline latencies of untreated/naive mice at P7. However, GH did not affect baseline withdrawal latencies to 40° C. (see FIG. 9; p<0.05; not shown). This effect did not however alter the results found at the various time points post inflammation. In other words, these alterations in baseline at the early age cannot account for the apparent beneficial effects of GH after injury as effects on baseline responses were only found at P7 and not P14 (see FIG. 9).

Figure 11:
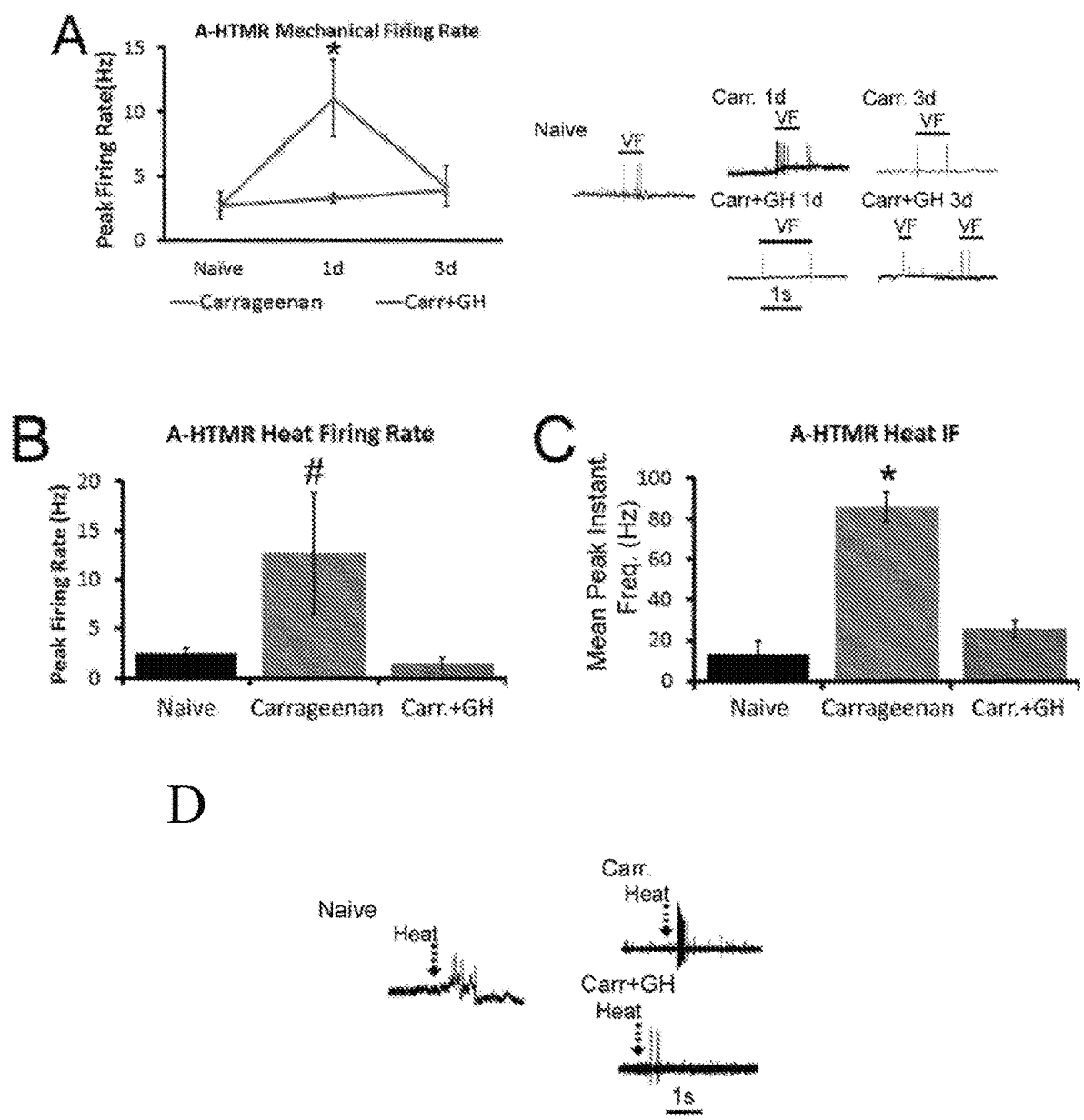
FIG. 11. Growth hormone (GH) pretreatment blocks hypersensitivity of "A"-fiber sensory neurons to mechanical and thermal stimuli during cutaneous inflammation initiated at P7 as assessed with ex vivo recording. Panel A: At P7, carrageenan injection into the hairy hindpaw skin was found to increase the firing of mechanically sensitive and sometimes heat sensitive A-fiber nociceptors (11A-high threshold mechanoreceptor: A-HTMR) one day post inflammation; however, this was completely blocked by GH pretreatment. In fact, responses of A-HTMRs to mechanical stimuli did not change relative to naïves at any time point post inflammation. Panel B, Panel C: Similar results on firing rate (Panel B) and mean peak instantaneous frequencies (Panel C) to heat were found in these cell types at P7 when combining data from both time points (1d and 3d). Examples of corresponding responses to various stimuli are presented with each panel(s). Recordings associated with Panels B and C are shown in Panel D. VF=von Frey filament (peak response for cell). *p<0.05 vs. naïve; # p<0.07 vs. naive; One-way ANOVA on Ranks/Dunn's post hoc.

When assessing the response properties of primary afferents using ex vivo recording in these P7 cohorts, Applicant found that A-HTMR peak mechanical FRs were increased (n=10; p<0.05) at 1d post inflammation compared to naive cells (n=7). However, GH pretreatment in the inflamed mice produced mechanical responsiveness similar to naïve levels at 1d (n=7, p>0.05). No differences in mechanical firing were found between the groups at 3d (FIG. 11, Panel A; Inflammation Only: n=5; Inflammation+GH: n=15). Although peak heat FRs were increased in A-HTMR neurons after carrageenan injection, this did not reach statistical significance (p<0.1). Peak heat IFs however, were found to be increased in "A"-fiber nociceptors (n=3) 1d after carrageenan injection into the hairy skin (FIG. 11, Panel B; p<0.05). GH also appeared to restore heat firing; however, Applicant were only able to record from one heat responsive A-fiber at 1d and one A-fiber at 3d in these mice. Therefore, Applicant combined data from both time points to try to obtain at least some basic information regarding heat hypersensitivity in A-fiber HTMR neurons from inflamed mice treated with GH. When combining both time points, GH pretreatment was found to prevent inflammation induced heat hypersensitivity in A-HTMRs during P7 inflammation (n=2; FIG. 11, Panel B, C). The mechanical and heat FRs in the CPM and CM neurons displayed no obvious changes post-inflammation at P7 and these were also unaffected by GH treatment (CPM: n=4-17 (mechanical), n=4-11 (heat); CM: n=5-9; $p>0.05$, not shown). Similar results were also found even if all C-HTMRs were combined (CM and CPM; n=11-23; $p>0.05$), thus supporting the notion that alterations in primary afferents during P7 cutaneous inflammation is restricted to sensitization in the faster conducting, broad spiking sensory neurons (A-fiber nociceptors), but a GH pretreatment can potentially block these effects. The average CVs for A-fibers were 4.04 m/s and average CVs for C-fibers were 0.52 m/s at P7.

Figure 12:
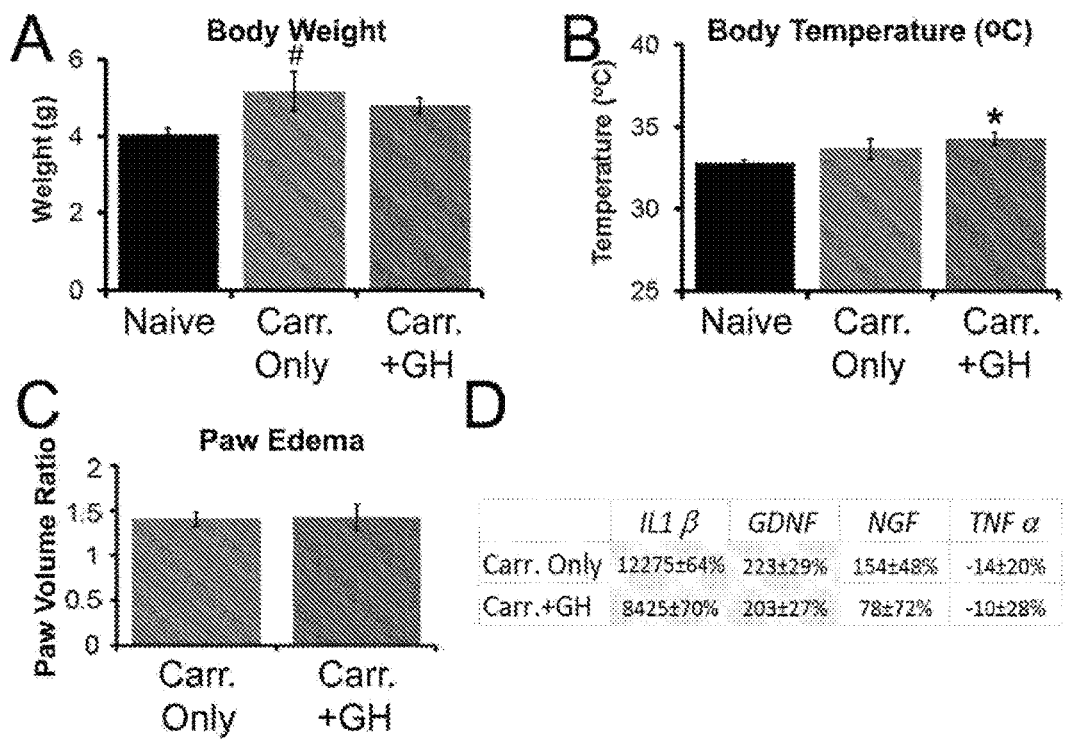
FIG. 12. Effects of GH pretreatment on body weight, temperature, paw edema and mRNA expression of select cytokines and growth factors in skin post inflammation at P7. Panel A, Panel B: GH pretreatment had no overt effects on body weight (Panel A) or body temperature (Panel B) post treatment (1-3d) in mice with inflammation at P7. Although mice with inflammation only showed a slight increase in body weight from carrageenan injection relative to naïve animals, this was not found to be different than mice treated with GH (p>0.05). GH treated mice with inflammation were also not found to be different than naives at P7. Although no effects of inflammation were found on body temperature at P7, pretreatment of mice with GH showed a slight increase in body temperature that was different than naives, but not different than mice with carrageenan injection alone. * p<0.05 vs. naïve but not Carr. only; #p<0.05 vs. naïve, but not Carr.+GH treated mice; n=4-14/ group; One-way ANOVA/Holm Sidak post hoc. Panel C: Carrageenan induced paw edema was unaffected by GH pretreatment. Values presented represent the paw volume ratio between ipsilateral and contralateral hindpaws. Panel D: Of the cytokines and growth factors found to be detected in skin of neonates after inflammation, the carrageenan induced upregulation of interleukin 1β (IL1β and glial cell line-derived neurotrophic factor (GDNF) were not altered by GH pretreatment. Although each group showed enhanced expression in skin relative to naives, this increase in gene expression was not found to be different from each other. No changes in nerve growth factor (NGF) or tumor necrosis factor α (TNFα were found in the skin in any group relative to naïves. n=3-4; One-way ANOVA/Tukey's post hoc. Values are presented as a percent change from naïve.

When assessing other potential effects of GH on the P7 groups, Applicant detected a small increase in body weight in P7 mice injected with carrageenan only, but GH had no effects on body weight in inflamed mice. A small increase in body temperature at P7 in inflamed mice treated with GH relative to naïve was found ($p<0.05$), however the temperatures in these mice were not different than mice that received carrageenan alone (FIG. 12, Panel A), B; n=4-12; $p>0.05$). At P7, carrageenan induced a similar level of paw edema in mice with GH pretreatment to that observed in mice with carrageenan injection alone (FIG. 12, Panel C). Finally, significant increases in cutaneous IL1β and GDNF were found in inflamed mice vs. naives at P7, but GH had no effects on the inflammation-induced upregulation of these factors in the skin. No changes in NGF or TNFa were found in the skin after P7 cutaneous inflammation and GH did not alter this result (FIG. 12, Panel D).

Figure 5:
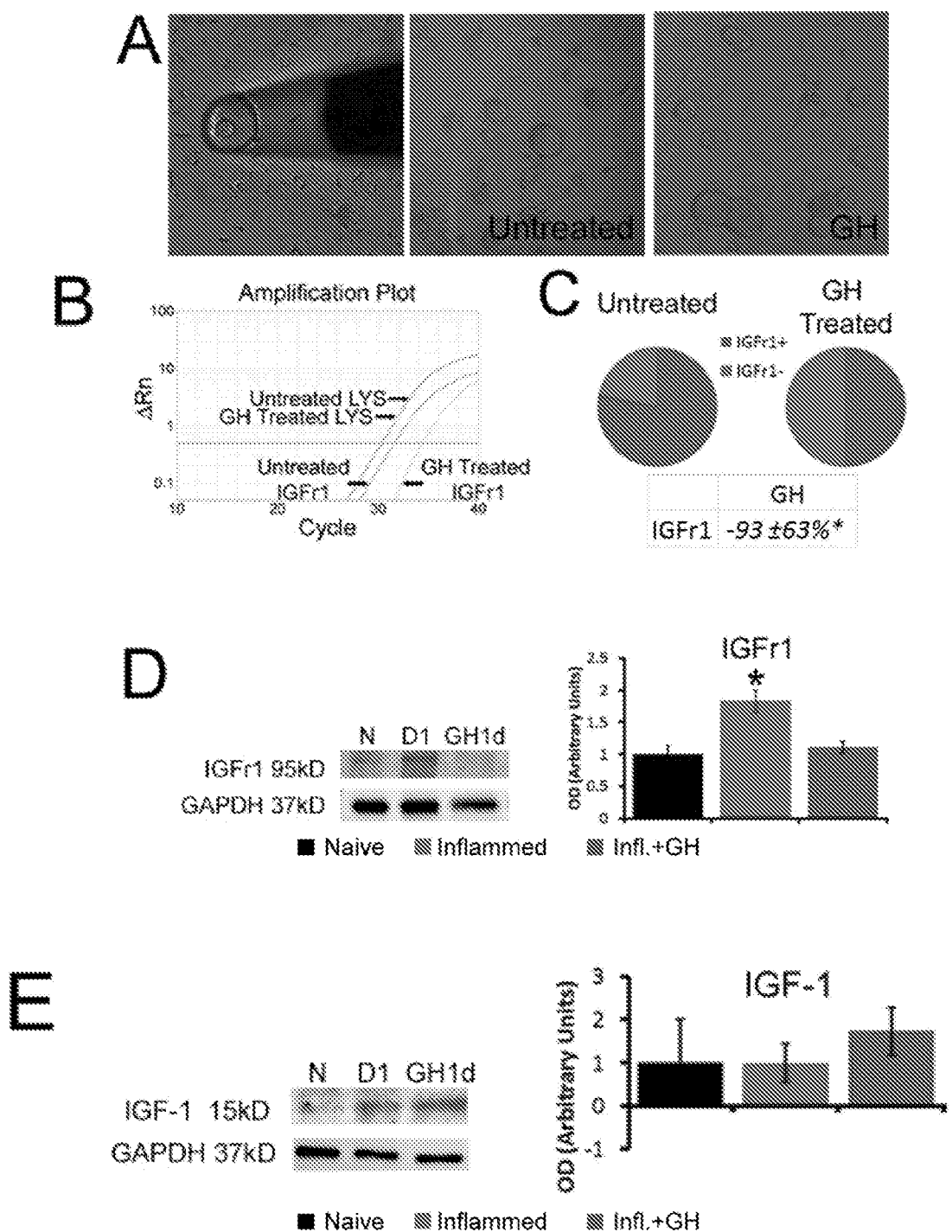
FIG. 5: Growth hormone (GH) regulates the expression of insulin like growth factor 1 receptor in vitro and after inflammation in vivo at P14. Examples of the single cell collection method used for analysis and examples of primary dorsal root ganglion (DRG) cultures treated with or without GH (Panel A). Single cell PCR results from the various culture conditions show that treatment of primary P14 DRG neurons (n=20) with GH significantly reduces the expression of IGFr1 in single cells (Panel B, Panel C). Example of an amplification plot obtained from a cell treated with GH compared to an untreated DRG neuron shows a rightward shift in the Ct value for IGFr1 in the GH treated neuron while the LYS normalization control gene remained constant in each cell (Panel B). In addition to significantly reduced relative expression, the number of cells that express IGFr1 (IGFR1+) at detectable levels in GH treated cultures was also lower than the number of cells containing IGFr1 in untreated DRG neuron cultures (Panel C). One day (D1) after carrageenan induced inflammation of the hairy hindpaw skin, a significant increase in IGFr1 protein is detected in the DRGs; however this is completely prevented in mice treated with GH at P14 (Panel D; n=3-4 for each age). No changes in the ligand IGF-1 however, were detected in the skin among any of the experimental groups tested (Panel E; n=3-4). Examples of IGFr1 and IGF-1 western blots along with their GAPDH are provided in panels 5D and 5E. * $p<0.05$ vs. naïve (N); One-way ANOVA/Tukey's post hoc test. Value in Panel C is presented as a percent change from naïve.

GH regulates the expression of IGFr1 in sensory neurons. Applicant next investigated potential downstream receptor mechanisms within sensory neurons underlying GH effects. Applicant therefore first performed realtime PCR on the L2/L3 DRGs from mice with cutaneous inflammation. Applicant surprisingly did not detect any differences in the expression of the GH receptor (GHr) in the DRGs of mice inflamed at P7 (−30.6±13%) or P14 (−40.7±23.3%) compared to age-matched naïve DRGs ($p>0.05$). Applicant's previous data showed a significant increase in IGFr1 at both ages, which is a known downstream mediator of GH function in other systems and has also been linked to mechanical and thermal hypersensitivity after inflammation. Therefore, to test if GH regulated the expression of IGFr1 specifically in sensory neurons, Applicant dissociated P14 DRGs and treated individual cultures with growth hormone. PCR analysis of single DRG neurons (n=20) showed that treatment of primary cultures with GH not only reduced the numbers of individual cells that expressed IGFr1, but the cells that contained IGFr1 in the GH treated cultures showed significantly reduced expression of this receptor ($p<0.05$) compared to untreated neurons (FIG. 5, Panels A-C). Using WB, Applicant found that carrageenan induced an increase in IGFr1 protein in the DRGs of mice at P14. This increase however, was blocked by pretreatment with GH (FIG. 5, Panel D). Interestingly, Applicant found no changes in IGF-1 in the skin from any group (FIG. 5, Panel E). These data suggest that IGFr1 may be one target by which GH could regulate peripheral hypersensitivity within sensory neurons during neonatal cutaneous inflammation.

Primary afferent knockdown of IGFr1 blocks peripheral hypersensitivity and alterations in sensory neuron response properties during neonatal cutaneous inflammation. Based on the above information, Applicant then utilized a nerve-specific siRNA mediated knockdown strategy to specifically inhibit the inflammation induced upregulation of IGFr1 in injured saphenous afferents. IGFr1 expression in the DRGs (n=6-14) of mice injected with non-targeting siRNAs (si-CON) plus inflammation confirms Applicant's previous report of a significant increase in IGFr1 mRNA 1d after inflammation at P14 (95.3%±14.8%; $p<0.05$ vs naïve). Injection of IGFr1 targeting siRNAs (siIGFr1) in inflamed mice prevented this increase (49.7%±14.9%; $p>0.05$). WB results (n=3-4) also shows that siIGFr1 injection successfully blocked the inflammation-induced increase in IGFr1 protein in the DRGs ($p<0.05$, FIG. 6A).

Figure 13:
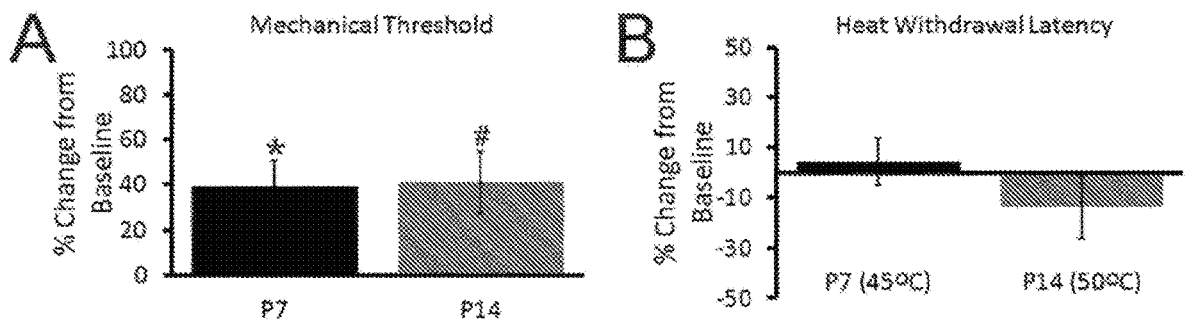
FIG. 13. Behavioral effects of siRNA (siCON) injection on mechanical and heat withdrawal responses in P7 or P14 neonates. Panel A: Injection of non-targeting control siRNAs (siCON) into un-inflamed mice (no carrageenan) slightly elevated mechanical withdrawal thresholds to von Frey filament stimulation of the hairy skin at P7, but this subtle increase in mechanical thresholds did not reach statistical significance at P14. Panel B: No effects of siRNA injection were detected in regards to heat withdrawal latencies to 45° C. (P7) or 50° C. (P14) water relative to their baseline measurements at either age tested. *p<0.05 and #p<0.07 vs. baseline; One-way ANOVA with Holm-Sidak post hoc.

Applicant then assessed behavioral hypersensitivity during cutaneous inflammation, in addition to afferent sensitization at P14. Ipsilateral hindpaw mechanical thresholds at 1d post inflammation were again decreased from baseline in the siCON+Carrageenan group (n=11; $p<0.05$), while in the siIGFr1 +carrageenan group (n=10), the thresholds only partially decreased from their baseline ($p<0.05$, FIG. 6, Panel B). Again no changes were found in the contralateral limbs in any group at 1d (not shown). At 50° C., the heat withdrawal latencies were significantly decreased from baseline in the siCON group ($p<0.05$), but no significant changes were found in the siIGFr1 injected mice with inflammation ($p>0.05$, FIG. 6 Panel C, D). The heat withdrawal latencies at 45° C. were not different between baseline and 1d inflammation for either siRNA injected group at P14 (not shown). No effects of siCON injection were detected in regard to mechanical sensitivity in mice at P14. The siRNA injection strategy also did not alter behavioral responses to heat stimulation (FIG. 13).

Single unit recording using ex vivo preparation showed no differences in mice with siCON injection plus carrageenan compared to mice that only received carrageenan injection (Table 1), therefore data from these two groups were combined to enhance statistical power. At P14, CPM mechanical FRs (n=14), heat FRs and heat IFs (n=12) all increased in the siCON group ($p<0.05$) after carrageenan compared to naïves (n=10 (mechanical) and n=7 (heat)). siIGFr1 injection prevented the inflammation induced alterations in the CPM neurons at this age (n=15 (mechanical) and n=11 (heat); $p>0.05$, FIG. 6, Panel D-F). Similar effects of IGFr1 knockdown were found on the CM neurons at this age in regard to the mechanical FRs (Naïve: 1.8±0.3 Hz, n=8; siCON+carrageenan: 4.9±0.7 Hz, n=12, $p<0.05$ vs. naive; siIGFr1 +carrageenan: 3.5±0.6 Hz, n=6, $p>0.05$ vs. naive). A-HTMR mechanical FRs, however, were not different between any group (n=6-15; not shown); Finally, Applicant was only able to record from one A-fiber that responded to heat at P14 from each of the siCON and siIGFr1 groups, thus Applicant was unable to assess the effects of IGFr1 knockdown on A-fiber heat responses at this age.

TABLE 1

Comparison of the response properties of A-HTMRs, CPM or CM fibers in mice at P7 or P14 with hairy skin inflammation alone or those with siCON injection plus inflammation as assessed with ex vivo recording. No differences detected.

| | Mechanical Thresholds | | Mechanical Firing Rates | | Heat Thresholds | | Heat Firing Rates | |
|---|---|---|---|---|---|---|---|---|
| | 1 d Inflammation | siCON + Infl. | 1 d Inflammation | siCON + Infl. | 1 d Inflammation | siCON + Infl. | 1 d Inflammation | siCON + Infl. |
| P7 | | | | | | | | |
| A-HTMR | 47.6 ± 14.6 | 34.6 ± 7.2 | 11.1 ± 3.0 | 6.3 ± 1.0 | nt | 39.9 ± 6.7 | 12.7 ± 6.2 | 8.3 ± 2.6 |
| CPM | 24.6 ± 12.6 | 28.5 ± 7.6 | 6.5 ± 1.3 | 4.2 ± 0.9 | 45.9 ± 0.9 | 45.8 ± 1.4 | 1.5 ± 0.3 | 2.2 ± 0.3 |
| CM | 57.5 ± 12.6 | 31.6 ± 7.1 | 4.2 ± 1.6 | 3.6 ± 0.5 | nt | nt | nt | nt |
| P14 | | | | | | | | |
| A-HTMR | 19.5 ± 7.5 | 37.8 ± 21.5 | 9.0 ± 1.3 | 6.9 ± 1.5 | 47.5 | 45.6 | nt | nt |
| CPM | 15.4 ± 7.8 | 29.8 ± 9.2 | 5.9 ± 0.3 | 5.7 ± 0.3 | 40.3 ± 4.0 | 42.1 ± 1.9 | 6.0 ± 2.5 | 6.2 ± 1.9 |
| CM | 41.3 ± 7.2 | 42.0 ± 13.9 | 4.3 ± 0.8 | 5.3 ± 1.0 | nt | nt | nt | nt |

Figure 14:
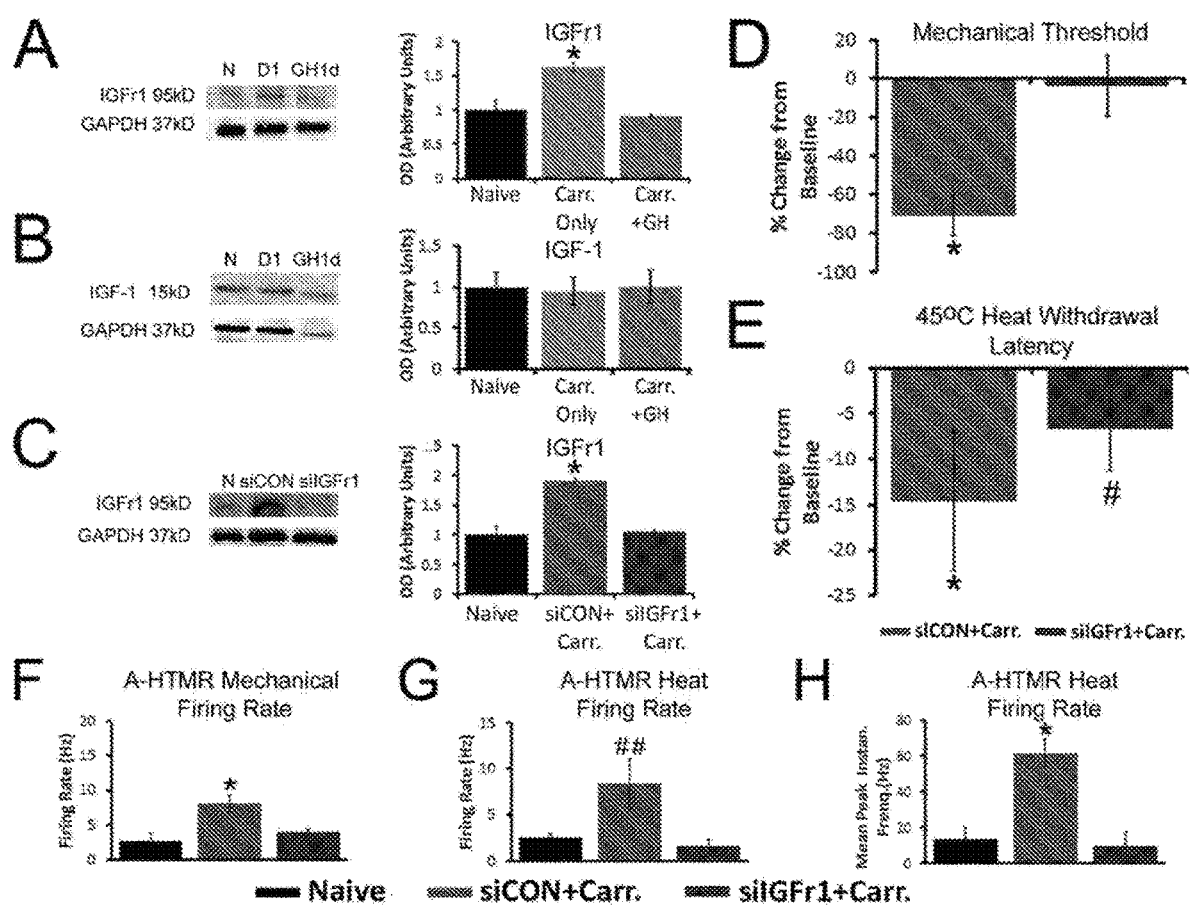
FIG. 14. Effects of GH on IGFr1/IGF-1 protein levels and consequences of nerve specific inhibition of IGFr1 on mechanical and heat responsiveness during P7 cutaneous inflammation. Panel A: Western blot results show that at P7, hairy hindpaw skin inflammation induces a significant increase in IGFr1 protein in the DRGs that can be inhibited by GH pretreatment. Neither carrageenan injection nor GH pretreatment in P7 inflamed neonates alters the levels of IGF-1 protein in the skin. Panel C: Saphenous nerve injection of siRNAs targeting IGFr1 (siIGFr1) successfully blocks the increase in IGFr1 expression found in the DRGs of mice with saphenous nerve injection of control, non-targeting siRNAs (siCON) and hairy skin carrageenan injection at P7. Panels A-C: Example western blots of IGFr1, IGF-1 and GAPDH are provided from each condition (n=3-4/group). Panel D: siIGFr1 injection completely prevented the carrageenan (Carr.) induced decrease in ipsilateral mechanical paw withdrawal thresholds 1d after cutaneous inflammation (siCON+Carr). siIGFr1 injection also inhibited the inflammation-induced reduction in heat withdrawal latency at 45° C. (E). Panels F-G: siIGFr1 (n=4 (mechanical) and n=3 (heat)) reversed the inflammation (siCON+Carr) induced increase in A-fiber high threshold mechanoreceptor (A-HTMR) mechanical (n=28) firing rates (Panel F), heat (n=9) firing rates (Panel G) and mean peak instantaneous frequencies (IF) to heat (Panel H) 1d after carrageenan injection into the hairy hindpaw skin. (naïve: n=7, mechanical; n=2, heat). *p<0.05 vs. naïve or baseline; #p>0.05 vs. baseline and siCON; ##p<0.069 vs. siIGFr1+Carr. Panel A-Panel E: One-way ANOVA with Tukey's or Holm-Sidak post hoc; Panel F-Panel G: Kruskal Wallis with Dunn's post hoc.
Figure 15:
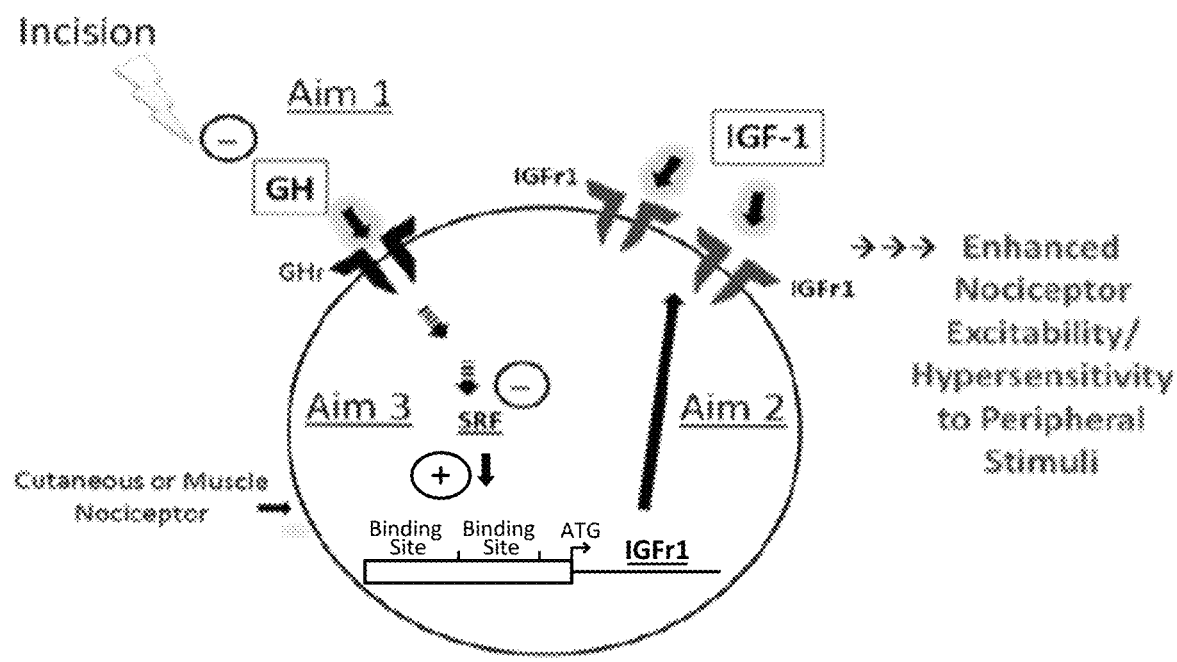
FIG. 15. Central hypothesis on the role of growth hormone (GH) in mediating neonatal incision pain. Without intending to be limited by theory, growth hormone levels normally limit the afferent expression of insulin-like growth factor receptor type 1 (IGFr1) through tonic inhibition of SRF dependent transcription. Under conditions of cutaneous and muscle incision, GH levels are inhibited in these peripheral tissues resulting in a disinhibition of SRF mediated transcription and thus a compensatory upregulation of IGFr1 in nociceptors. This upregulation leads to enhanced excitability in sensory afferents to peripheral stimuli, as the unaffected IGF-1 levels in the periphery can act on more receptors. This is believed to ultimately modulate ongoing pain, thermal and mechanical sensitivity, and muscle function after neonatal peripheral injury.

In order to again assess whether similar effects of GH could be found on IGFr1 expression or whether nerve specific IGFr1 inhibition could also blunt peripheral hypersensitivity found in younger neonates with inflammation, Applicant performed similar experiments described above in these younger cohorts. As was found with P14 inflammation, P7 carrageenan injection upregulated IGFr1 in the DRGs, which was prevented by GH pretreatment, but inflammation did not alter cutaneous IGF-1 levels (FIG. 14; n=3-4). In addition, siRNA mediated knockdown of IGFr1 in sensory neurons prevented the development of pain-related hypersensitivity (n=9-10), and the sensitization of A-HTMRs, normally seen after P7 inflammation (FIG. 14). siCON injection alone slightly increased mechanical thresholds at P7, but did not alter heat (45° C.) withdrawal latencies (see FIG. 13). These data suggest that afferent selective knockdown of IGFr1 blocks peripheral hypersensitivity and alterations in sensory neuron response properties during neonatal cutaneous inflammation similar to GH pretreatment.

Discussion

Growth hormone and nociceptor sensitization. The initial postnatal period of life is a critical stage for the development of the peripheral nervous system, and early life injury produces long-term alterations in nociceptive processing. Pain also occurs after injury in pediatric patients at all ages and related effects in developing mice after injury were observed (FIG. 2, FIG. 10). Furthermore, insults sustained during development induce patterns of sensory neuron sensitization that differ from those seen in adults. Thus the specific mechanisms by which pain may develop in neonates could be unique.

Figure 6:
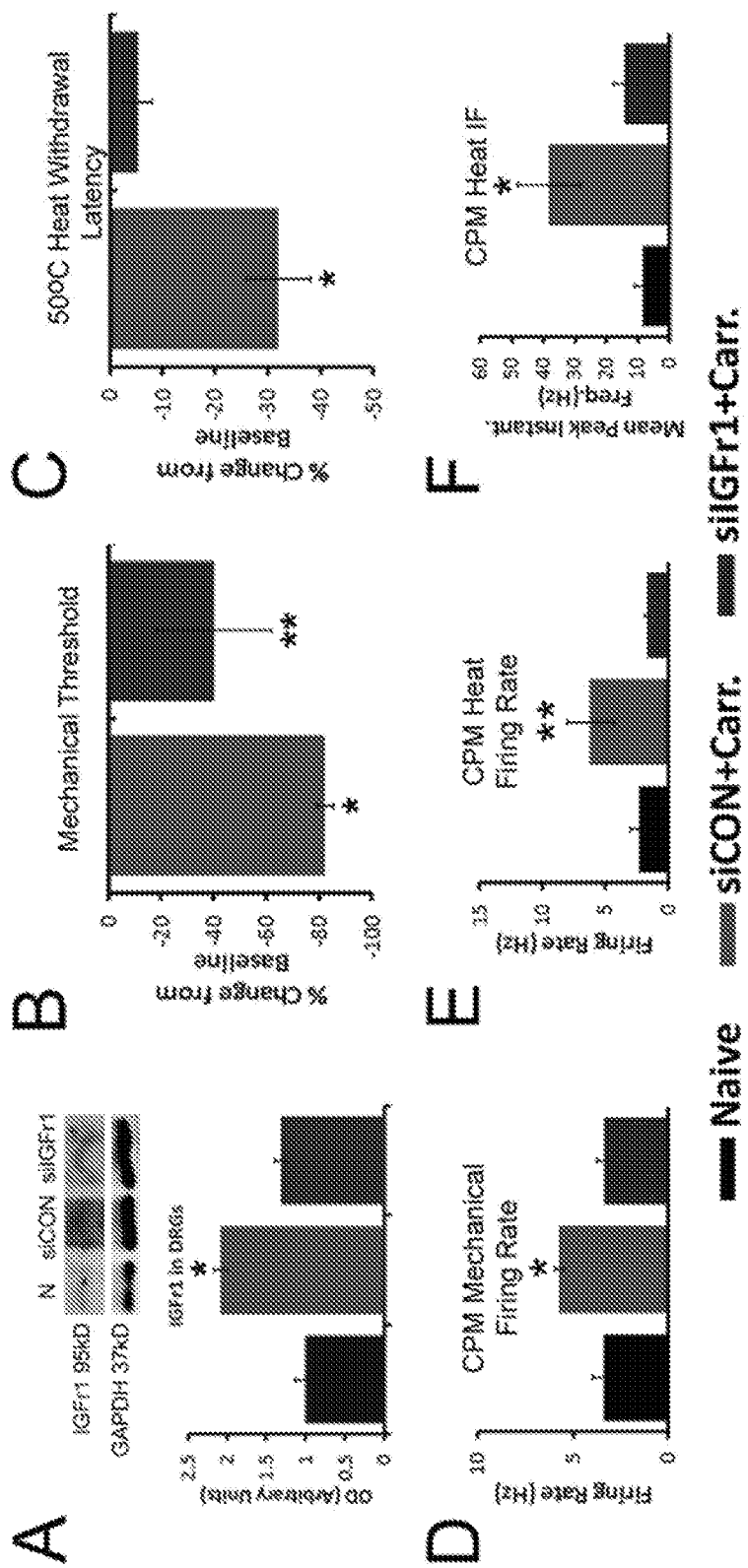
FIG. 6: Selective insulin like growth factor 1 receptor (IGFr1) knockdown inhibits mechanical and heat hypersensitivity during inflammation at P14. Panel A: Western blot results show that saphenous nerve injection of siRNAs targeting IGFr1 (siIGFr1) successfully blocks the increase in IGFr1 expression found in the DRGs of mice with saphenous nerve injection of control, non-targeting siRNAs (siCON) in addition to hairy skin carrageenan injection at P14 (n=3-4/group). Example western blots of IGFr1 and GAPDH are provided from each condition. Panel B: At P14, siIGFr1 partially reversed the carrageenan induced reduction in ipsilateral mechanical withdrawal thresholds 1d after inflammation. Panel C: The inflammation induced decrease in heat withdrawal latency at 50° C. was completely blocked by siIGFr1 injection. Using ex vivo recording, the inflammation induced increase in polymodal "C"-fiber (CPM) neuron firing rates to both mechanical (Panel D) and heat (Panel E) stimuli and the mean peak instantaneous frequencies (IFs) to heat (Panel F) were all blocked by afferent targeted IGFr1 siRNAs during inflammation. Results are consistent to that described for GH treatment above. Panel A-Panel C: * $p<0.05$ vs. naïve or baseline; **$p<0.05$ vs. baseline and 1d siCON+Carr.; One-way ANOVA with Holm Sidak or Tukey's post hoc tests. Panel D-Panel F: *$p<0.05$ vs. Naïve and siCON+Carr.; **$p<0.05$ vs. siIGFr1+Carr. and $p<0.06$ vs. naïve; One-way ANOVA on Ranks/Dunn's post hoc.

Here Applicant found that cutaneous inflammation in neonatal mice produced a transient reduction in GH levels selectively in the affected skin, which corresponded with the development and resolution of mechanical and thermal hypersensitivity during inflammation. Pretreatment of inflamed neonatal mice with exogenous GH prevented this hypersensitivity and blocked all of the injury-induced alterations in cutaneous afferents (FIG. 1-3, FIG. 10-11), possibly by preventing the upregulation of IGFr1 within sensory neurons (FIGS. 5, 6, 14).

Children with GHD display a resting pain, which suggests that GH levels may have robust effects on sensory function during early life when the peripheral nervous system is undergoing normal functional and neurochemical changes. During development, sensory neurons change their phenotype as myelinated afferents lose heat sensitivity during the first week of life while "C"-fibers gain heat sensitivity during the second week. NGF and GDNF likely play a role in this normal phenotypic switch in addition to afferent sensitization after injury. However, the data also suggests that GH may be one additional factor involved in shaping sensory responsiveness specifically in regards to how the afferents respond to neonatal injuries and generate a pain state (FIGS. 1-3; FIGS. 9, 11).

Interestingly, Applicant observed an effect of GH on normal behavioral responses at P7 specifically. GH pretreatment reduced mechanical thresholds and increased heat withdrawal latencies in uninjured mice only at P7 (FIG. 9). This change in mechanical and thermal sensitivity in the P7 mice essentially produced thresholds/latencies that were similar to naive P14 mice. As GH levels are known to increase over time during early life to enhance normal growth and development, artificial delivery of GH to a very young mouse may hasten the development of the peripheral sensory system even under conditions in which very low doses are used. However, the fact that these tests are performed on the hairy skin and not the glabrous skin may be another factor, as this technique becomes increasingly more difficult to perform as the animals get older. Regardless, mice treated with GH still displayed a complete block of mechanical and heat hypersensitivity provoked by cutaneous inflammation (FIG. 2, 10).

GH has well-documented effects on growth and metabolism and extended GH treatment in patients is known to produce side effects such as increased weight gain, transient fever or hyperglycemia. At the doses used to stimulate growth in GHD, GH would not be suitable to use in normal children due to metabolic and other side effects. Applicant found that a short course of low dose (0.5 mg/kg, ip.; 1x/d for 3d prior to inflammation) GH was able to reverse pain-like behaviors (FIG. 2, 10) induced by cutaneous inflammation without inducing classic side effects or growth promoting effects of extended GH delivery in mice, such as weight gain, transient fevers, and hyperglycemia. Furthermore, the GH pretreatment regimen did not alter paw edema during inflammation, nor was it able to block select cytokine/growth factor production (IL1β, GDNF) in the skin (FIGS. 4, 6; not shown). Although it unclear how GH is reduced in the periphery during inflammation, Applicant's data suggests that subtle changes in peripheral GH levels may have profound effects on sensory function after injury possibly via direct effects on the afferents (FIGS. 5, 6, 14). Future studies will be needed however to fully confirm this notion.

GH regulates afferent sensitization possibly by suppressing IGFr1 upregulation. The GHRH-GH-IGF-IGFr system is important for the development of body growth and repair after tissue injury. Similar to GH releasing molecules such as ghrelin or GHRH, IGF-1 and its receptor IGFr1, have also been demonstrated to be involved in nociceptive processing in adult rodents possibly by modulating neuronal excitability. Interestingly, in mice overexpressing IGF-2, studies have found reduced sensory innervation of the skin, which may play a role in peripheral responsiveness. Although Applicant did not assess IGF-2, significant alterations in IGF-1 in the skin during neonatal cutaneous inflammation was not detected, nor was transient, low dose GH therapy able to alter IGF-1 in the skin (FIG. 5, FIG. 14). However, Applicant did observe an upregulation of IGFr1 in the DRGs (FIG. 5, FIG. 14). IGFr1 is expressed in medium and small diameter DRG neurons, which are likely the cells that are experiencing sensitization during inflammation. Since GH can directly modulate the expression of IGFr1 in single primary afferent neurons (FIG. 5), Applicant sought to determine if IGFr1 upregulation was one possible mediator of the observed hyper-responsiveness within sensory neurons that was downstream of reduced GH levels in the skin. Similar to GH pretreatment, Applicant found that afferent selective knockdown of IGFr1 during neonatal inflammation also prevented the injury-induced alterations in cutaneous afferents in addition to mechanical and thermal hypersensitivity (FIG. 6, FIG. 14).

Mechanistically, this may due to the fact that GH can modulate IGFr1 transcription through one of the many of the transcription factors that are known to be activated by GH signaling such as serum response factor or ELK1. Each of these factors have binding sites in the upstream promotor region of IGFr1 (MatInspector software) and have been shown to act as transcriptional repressors under certain contexts, which could be at play in sensory neurons. Thus loss of GH could reduce the activation of the transcriptional repressors, subsequently permitting IGFr1 upregulation in the DRGs. IGFr1 would then have the ability to increase the responsiveness of DRG neurons to mechanical and thermal stimuli by modulating excitability or by regulating many of the transcription factors activated from IGFr1 signaling such as ELK-1, CREB, or NFAT [MatInspector] which can regulate the expression of various other sensory transduction receptors/channels (e.g. TRPM3, ASIC3, P2X3, TRPV1, Piezo2, etc) that are modulated during inflammation. While a loss of cutaneous GH may seem counterintuitive during injury since it is a known tissue repair molecule, the transient nature of this loss may serve a role in dynamic IGFr1 upregulation in the DRGs to subsequently modulate mechanical and thermal responsiveness (i.e. pain), which is itself a protective measure for tissue repair. Although the data do not completely confirm whether GH is acting directly or indirectly on the sensory neurons, one plausible mechanism by which GH acts within sensory neurons to mediate hypersensitivity to peripheral inflammation in neonates is via its effects on IGFr1 upregulation.

Clinical Significance. GH has been reported to be an effective pain therapy for GHD children and patients with erythromelalgia. Other reports have also shown that GH treatment is an effective pain therapy for patients with fibromyalgia. However the effect in fibromyalgia patients was mainly found in those with corresponding low IGF-1 levels. Applicant's data shows no effects of neonatal inflammation or GH treatment on IGF-1 in the skin (FIG. 5, FIG. 14). This may suggest that the link to IGF-1 levels and the effectiveness of a GH therapy may be specific to widespread muscle pain disorders in adults and not neonatal inflammatory pain states. Nevertheless, Applicant's results show GH has profound effects on injury responses during postnatal development, suggesting that a short course of low dose GH replacement therapy may eventually be used as an effective pharmacological treatment strategy for neonatal pain that does not cause unwanted side effects typically seen with extended GH delivery in humans. As neonatal injury is known to alter primary afferent function which can reorganize the developing DH if initiated at early ages, this strategy may also mitigate the long-term consequences of early life insult on adult nociceptive processing.

Example 2

In order to better understand how individual subpopulations of sensory afferents may contribute to pediatric pain states, Applicant recently developed neonatal hairy hindpaw skin/saphenous nerve and neonatal hindpaw muscle/tibial nerve/DRG/SC recording preparations to comprehensively phenotype cutaneous and muscle sensory neurons in mouse (FIG. 2). Using these preparations, Applicant's recent results show changes in afferent subtype prevalence during the course normal postnatal development that differ from adults. This suggests that only particular populations of afferents may have the ability to sensitize to specific modalities after peripheral injury at distinct ages further implying that unique primary afferent based mechanisms of pain generation may occur after injury at different ages.

Applicant has shown that the injury-evoked changes in afferent sensitivity in distinct subpopulations are age-dependent. In addition to preclinical data, Applicant's clinical data has shown that pediatric patients with the inflammatory skin disorder erythromelalgia or patients with fibromyalgia (who often display reduced systemic GH levels), that were treated with growth hormone (GH) were free of pain after treatment.

Applicant performed western blot (WB) analysis of GH and IGF-1 levels in hairy hindpaw skin or hindpaw muscles of P7 or P14 mice with cutaneous inflammation, skin incision, or muscle incision and compared this to age-matched naïve controls. Applicant found that both inflammation and incision produced a significant decrease in GH, ld after injury at P7 or at P14 with no effects on IGF-1 (FIG. 16.), suggesting that peripheral injuries produce GHD in the affected tissues. GHD was target specific, not systemic, and no changes to GH were found in the DRGs (not shown). Applicant thus pretreated mice (n=8-10) for three days with varing doses of GH (0.1-0.5 mg/kg; i.p.) prior to hairy skin inflammation at P7 or P14 and performed behavioral analyses for mechanical and thermal hypersensitivity. The maximum dose used in these experiments would be roughly half of the normal dose and $\frac{1}{12}$th of the duration required to reverse growth deficits in children or mice with GHD and has been shown not to induce a systemic effect on IGF-1 production. Applicant found that systemic GH treatment in this manner dose dependently inhibited inflammation induced mechanical and thermal hypersensitivity in neonates (not shown).

Figure 17:
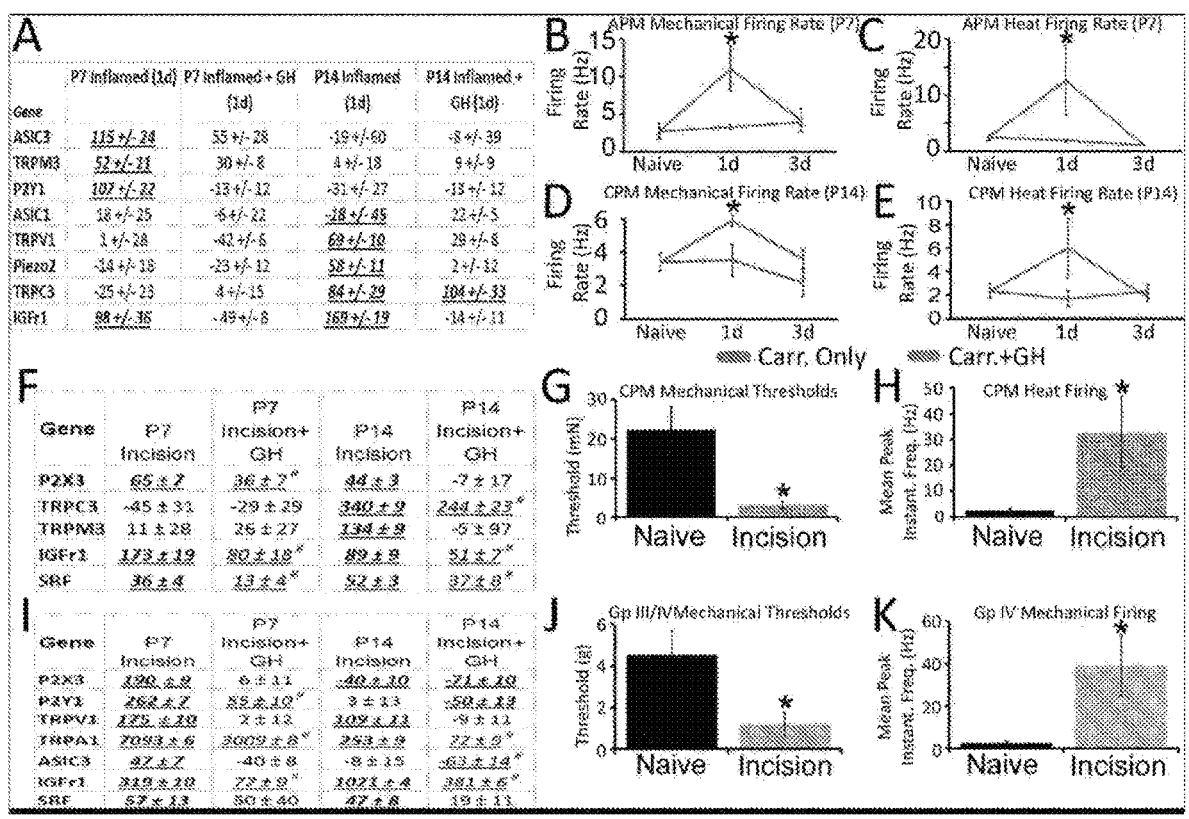
FIG. 17. Percent changes in gene expression in DRGs and changes in peripheral response properties in cutaneous or muscle afferents 1d after inflammation or incision at P7 or P14 with or without growth hormone (GH; 0.5 mg/kg66) pre-treatment. Panel A: Age specific upregulation of receptors/channels in L2/L3 DRGs after P7 or P14 skin inflammation. Myelinated, polymodal, high threshold mechanoreceptor (APM) firing rates (FRs) to mechanical (Panel B) and heat (Panel C) stimuli were increased at P7, and this was blocked by pretreatment of mice for 3d with GH. Inflammation also significantly reduced heat thresholds in the heat sensitive A-fibers (APM) at this age and this was also blocked by GH treatment (not shown). At P14, CPM FRs to mechanical (Panel D) and heat (Panel E) stimuli were increased compared to naives, but each of these changes in afferent function were also blocked by GH pretreatment. Numerous genes are unregulated in L2/L3 DRGs after P7 or P14 skin incision and these were all found to be either partially or fully blocked by GH pretreatment (Panel F). CPM neurons show decreased mechanical thresholds (Panel G) and increased firing to heat stimuli (Panel H) 1d after incision at P14. Note: Data presented here included cells (n=7) from one mouse at P27 to increase n, but data was not different from that at P14. Several genes are also unregulated in L4/L5 DRGs after P7 or P14 muscle incision vs nalves and these were all found to be partially or fully blocked by GH pretreatment (Panel I). Group III/IV neurons show decreased mechanical thresholds (Panel J) 1d after incision at P14, while group IV fibers specifically displayed enhanced firing to mechanical stimuli (Panel K). (Gene values: % Change vs. age-matched nalves). Underlined/bold/italics values in A, F and I=*p<0.05 relative to age matched naives. While underline/italics#=p<0.05 vs. naïve AND incision. B-E, G-H, J-K: *p value<0.05 vs. naive or Carr.+GH. K-W/Dunn's or ANOVA/Tukey's.
Figure 18:
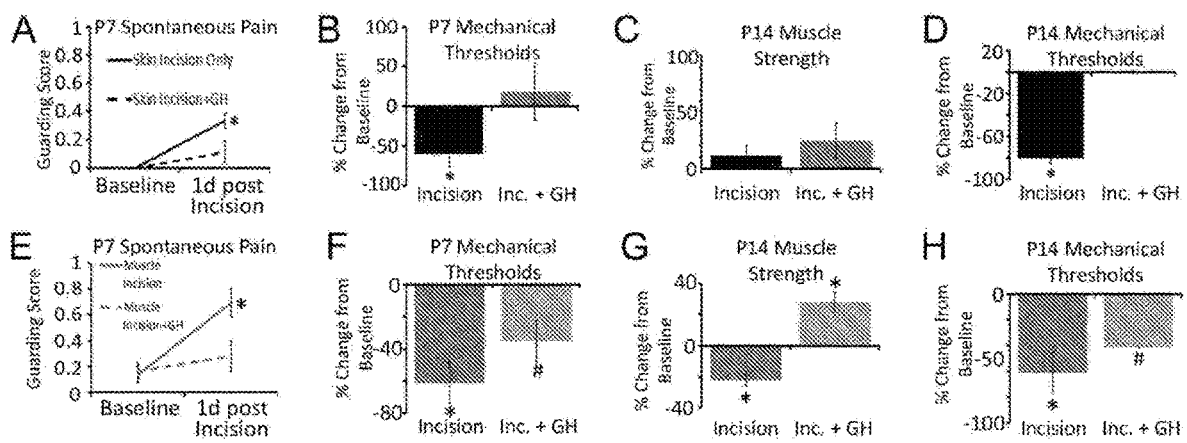
FIG. 18. Behavioral responses to cutaneous or muscle incision at P7 or P14 and the effects of GH treatment. Skin incision at P7 induces spontaneous guarding behaviors (A) and mechanical hypersensitivity (B) 1d after injury in the affected limb and this is blocked by GH treatment. No changes in muscle strength (C) are detected after skin incision at P14 vs. naives; however, mechanical hypersensitivity (D) found 1d after P14 incision is blocked by GH treatment. Muscle incision at P7 also induces spontaneous guarding behaviors (E) and mechanical hypersensitivity (F) 1d after injury in the affected limb and these are inhibited by GH treatment. Muscle incision specifically induced a significant reduction in muscle strength at P14 and GH therapy reversed this (G). Mechanical hypersensitivity found 1d after P14 incision however is partially blocked by GH treatment (H).*p value<0.05 vs. baseline; #p value<0.05 vs. baseline and 1d incision. 2-way RM ANOVA; Holm-Sidak or 1-way ANOVA; Tukey's.

Although this pretreatment strategy confirmed the viability of using GH to treat inflammatory pain in neonates, it does not often model the clinical situation in which the timing of injury is not known. However, in the context of surgery, it is known when the injury will take place, thus a pretreatment strategy is ideal for this scenario. In subsequent pilot experiments, Applicant found similar effects of GH (0.5 mg/kg; i.p) on incisional pain in P7 neonates (n=4-6) as Applicant found after inflammation in which guarding behaviors and mechanical hypersensitivity were reversed with GH pretreatment. This was observed after cutaneous incision only and skin plus muscle incision. Heat hypersensitivity in P7 mice was also blocked by GH treatment in both incision models (not shown). Since the slightly older (P14) mice (n=4-6) are able to perform grip strength testing, Applicant also wanted to determine if there was an effect of this injury model on a more muscle oriented task. While skin incision alone only reduced mechanical sensitivity, which was inhibited by GH treatment, muscle incision significantly reduced grip strength in addition to lowering mechanical thresholds in P14 mice. GH treatment inhibited both of these behavioral deficits at 1d after muscle incision at P14. There were no differences in heat sensitivity or guarding at this age, however. (FIG. 17)

While assessing the potential side effects of systemic GH treatment regimen, Applicant confirmed that treatment of naïve neonates (P7 or P14) with the maximal GH dose (0.5 mg/kg ip.) for three days prior to analyses did not alter baseline guarding, mechanical withdrawal thresholds or heat withdrawal latencies, with the exception of P7 neonates where Applicant found a small decrease in baseline mechanical thresholds (not shown).

Applicant performed realtime PCR and ex vivo recording experiments one day after P7 or P14 inflammation in mice pretreated with GH (0.5 mg/kg×3d) to determine if this factor could also alter DRG gene expression and functional changes in specific afferents that are likely mediators of ongoing pain and thermal and mechanical Hypersensitivity. Applicant first found that GH pre-treatment completely blocked almost all of the age specific, inflammation induced changes in DRG gene expression at both P7 and P14 (FIG. 17, Panel A) with the exception of TRPC382 83. Next Applicant found using ex vivo recording 1d after P7 inflammation (n=158 cells), that the increased firing to mechanical and heat stimulation of the skin in A-fiber polymodal (APM) neurons was fully blocked by GH pretreatment (FIG. 17, Panel B, C) with no rebound at 3d, which is also when Applicant normally observes a resolution of GH levels in the skin in non-GH treated mice (not shown). At P14, Applicant found similar effects of GH (n=152 cells) on inflammation induced afferent sensitization as the increases in both mechanical and heat responsiveness in C-fiber polymodal (CPM) neurons after P14 inflammation was inhibited by GH treatment (FIG. 17, Panel D, E, Jankowski M P, Ross J L, Weber J D, Lee F L, Shank A T, Hudgins R C. Age-dependent sensitization of cutaneous nociceptors during developmental inflammation. Mol. Pain. 10: 34. (2014). Thus GH may be altering mechanical and thermal hyperalgesia by blocking the injury induced changes in sensory neurons that initiate these pain behaviors. Since this GH regimen did not cause side effects, alter paw edema or vary cytokines in the skin during these acute time points, Applicant was able to study the effects of GH on afferent plasticity and gene expression separate from any "off-target" effects.

Figure 16:
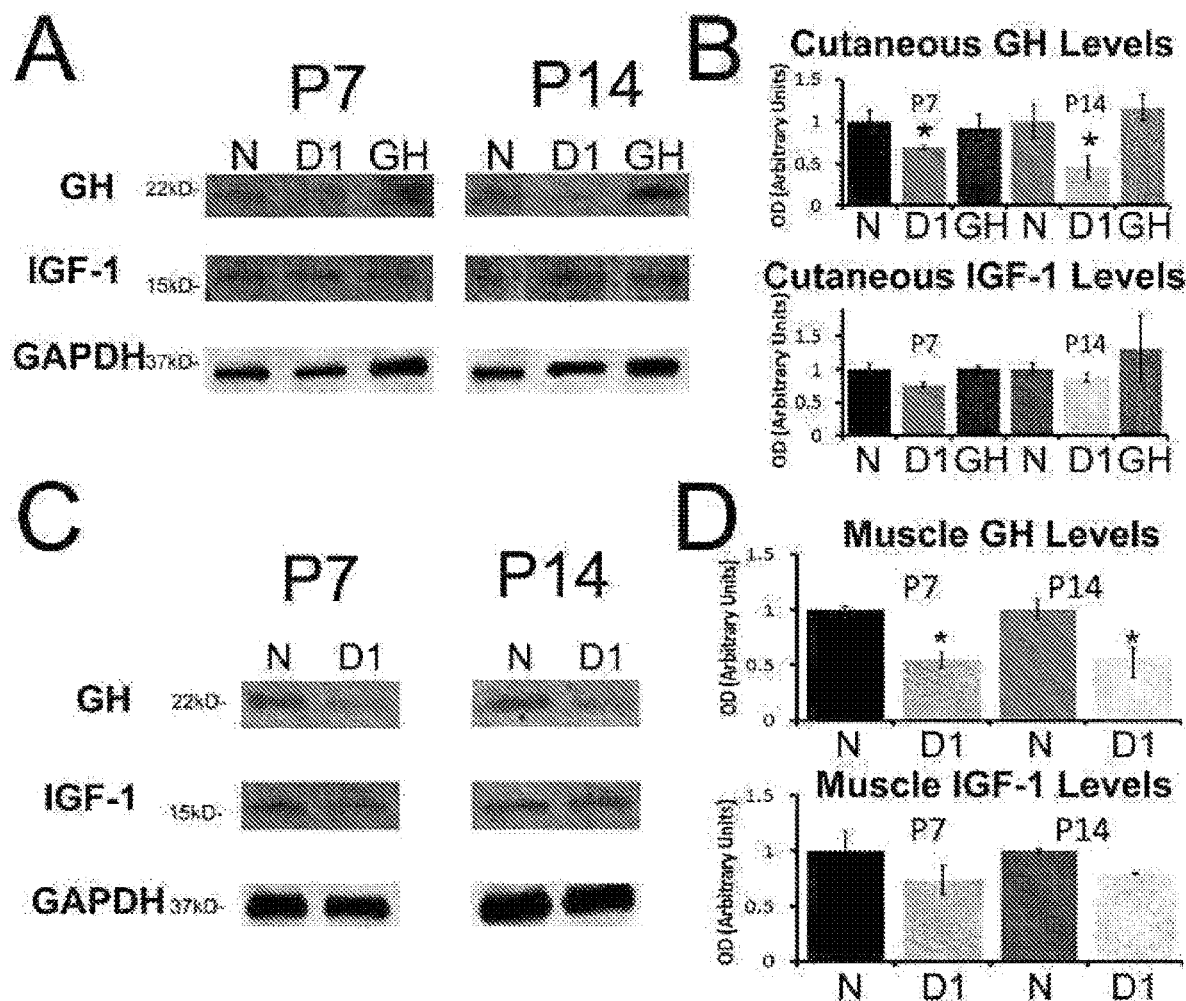
FIG. 16. Western blot analysis of hairy hindpaw skin or hindpaw muscles in naïve or incised mice at 1d with or without growth hormone (GH) treatment for GH, IGF-1 and GAPDH. Examples of reduced GH expression in hairy skin after cutaneous incision (A) at P7 and P14. GH protein levels (normalized to GAPDH) were significantly reduced in skin 1d post skin incision (B) and this is restored with exogenous GH treatment (0.5 mg/kg×3d). Similar results are found after muscle incision at both ages (C) in which quantification of GH levels show significant reduction 1d after muscle incision (D). No effects of incision or GH treatment were found on cutaneous or muscle IGF-1 levels. *p<0.05 vs naïves. 1-way ANOVA; Tukey's post hoc.

Applicant analyzed cutaneous and muscle afferent response properties with ex vivo recording from mice with cutaneous or muscle incision. With these experiments (n=63 cells) Applicant found that cutaneous incision at P14 reduced both mechanical thresholds (FIG. 16, Panel G) and heat thresholds (not shown) and the firing to heat stimuli in CPM neurons (FIG. 16, Panel H) 1d after incision. Applicant also confirmed that GH had pronounced effects on the age-dependent upregulation of receptors typically linked to nociceptive processing in the DRGs after skin incision (FIG. 16, Panel F). In mice with muscle incision, Applicant found specific reductions in mechanical thresholds in group III and IV muscle afferents as well as increased firing to cold stimuli (not shown) in these fibers 1d after muscle incision. Group IV fibers, were also specifically found to display enhanced firing to mechanical stimuli (FIG. 16, Panel J, K). These alterations in response properties again corresponded with specific upregulation of sensory transducers in the respective DRGs. GH treatment blocked the upregulation of these genes in DRGs after muscle incision similar to skin incision (FIG. 16, Panel 1).

Example 3

One of the more significant problems with early life injury is not only the pain that comes with the insult, but the long term consequences of such injuries later in life. In addition to the abovementioned data, we also performed studies to assess the utility of a single GH treatment during early life insult to prevent the known priming effects of such injuries on later life hypersensitivity to subsequent re-injury (n=8-12). Results indicate that young adult mice with cutaneous inflammation display a longer lasting hypersensitivity to mechanical and thermal stimuli if they experienced an early life injury (P7 inflammation) compared to mice that only received carrageenan as adults. However, delivery of GH (1.5 mg/kg, ip. lx) to neonates at the time of neonatal inflammation (no pre-treatment) was able to significantly block this priming effect in the older mice during inflammation in addition to blunting the late stage CPM neuron sensitization observed in mice with dual injury (FIG. 19).

REFERENCES

[1] Beland B F M. Influence of peripheral inflammation on the postnatal maturation of primary sensory neuron phenotype in rats. J Pain 2001; 2:36-45.

[2] Bennett R. Growth hormone in musculoskeletal pain states. Curr. Rheumatol. Rep. 2004; 6:266-273. doi:10.1007/s11926-004-0034-z.

[3] Bennett R M. Disordered growth hormone secretion in fibromyalgia: a review of recent findings and a hypothesized etiology. Zeitschrift für Rheumatol. 1998; 57 Suppl 2:72-6. Available: http://www.ncbi.nlm.nih.gov/pubmed/10025088. Accessed 28 Jul. 2016.

[4] Bjersing J L, Dehlin M, Erlandsson M, Bokarewa M I, Mannerkorpi K. Changes in pain and insulin-like growth factor 1 in fibromyalgia during exercise: the involvement of cerebrospinal inflammatory factors and neuropeptides. Arthritis Res. Ther. 2012; 14:R162. doi:10.1186/ar3902.

[5] Choi Y S, Cho H Y, Hoyt K R, Naegele J R, Obrietan K. IGF-1 receptor-mediated ERK/MAPK signaling couples status epilepticus to progenitor cell proliferation in the subgranular layer of the dentate gyrus. Glia 2008; 56:791-800.

[6] Chong P K K, Jung R T, Scrimgeour C M, Rennie M J, Paterson CR. Energy expenditure and body composition in growth hormone deficient adults on exogenous growth hormone. Clin. Endocrinol. (Oxf). 1994; 40:103-110. doi: 10.1111/j.1365-2265.1994.tb02451.x.

[7] Cimaz R, Rusconi R, Fossali E, Careddu P. Unexpected healing of cutaneous ulcers in a short child. Lancet (London, England) 2001; 358:211-2. doi:10.1016/S0140-6736(01)05413-7.

[8] Craner M J, Klein J P, Black J a, Waxman S G. Preferential expression of IGF-I in small DRG neurons and down-regulation following injury. Neuroreport 2002; 13:1649-52. doi: 10.1097/00001756-200209160-00016.

[9] Cuatrecasas G, Alegre C, Casanueva FF. GH/IGF1 axis disturbances in the fibromyalgia syndrome: is there a rationale for GH treatment? Pituitary 2014; 17:277-83. doi:10.1007/s11102-013-0486-0.

[10] Cuatrecasas G, Gonzalez M J, Alegre C, Sesmilo G, Fernandez-Sold J, Casanueva FF, Garcia-Fructuoso F, Poca-Dias V, Izquierdo J P, Puig-Domingo M. High prevalence of growth hormone deficiency in severe fibromyalgia syndromes. J. Clin. Endocrinol. Metab. 2010; 95:4331-7. doi:10.1210/jc.2010-0061.

[11] Elitt C M, McIlwrath S L, Lawson J J, Malin S a, Molliver D C, Cornuet P K, Koerber H R, Davis B M, Albers K M. Artemin overexpression in skin enhances expression of TRPV1 and TRPA1 in cutaneous sensory neurons and leads to behavioral sensitivity to heat and cold. J. Neurosci. 2006; 26:8578-8587.

[12] Farris G M, Miller G K, Wollenberg G K, Molon-Noblot S, Chan C, Prahalada S. Recombinant rat and mouse growth hormones: risk assessment of carcinogenic potential in 2-year bioassays in rats and mice. Toxicol. Sci. 2007; 97:548-61. doi:10.1093/toxsci/kfm059.

[13] Fitzgerald M, Beggs S. Book Review: The Neurobiology of Pain: Developmental Aspects. Neurosci. 2001; 7:246-257. doi:10.1177/107385840100700309.

[14] Fred M. Sc. FANZC. S, Simon Ph.D. B, Ph.D. WSMMBBS. Targeting p38 Mitogen-activated Protein Kinase to Reduce the Impact of Neonatal Microglial Priming on Incision-induced Hyperalgesia in the Adult Rat. Anesthesiology 2015; 122:1377-1390.

[15] Garcia J M, Cata J P, Dougherty P M, Smith R G. Ghrelin prevents cisplatin-induced mechanical hyperalgesia and cachexia. Endocrinology 2008; 149:455-60. doi:10.1210/en.2007-0828.

[16] Gartner M H, Benson J D, Caldwell M D. Insulin-like growth factors I and II expression in the healing wound. J. Surg. Res. 1992; 52:389-394.

[17] Goodrich C A. Measurement of body temperature in neonatal mice. J. Appl. Physiol. 1977; 43:1102-5. Available: http://www.ncbi.nlm.nih.gov/pubmed/606696.

[18] Herndon D N, Hawkins H K, Nguyen T T, Pierre E, Cox R, Barrow R E. Characterization of growth hormone enhanced donor site healing in patients with large cutaneous burns. Ann. Surg. 1995; 221:649-56; discussion 656-9. Available: http://www.pubmedcentral.nih.gov/articlerender.fcgi?artid=1234688&tool=pmcentrez&rendertype=abstract.

[19] Jankowski M P, Cornuet P K, McIlwrath S, Koerber H R, Albers K M. SRY-box containing gene 11 (Sox11) transcription factor is required for neuron survival and neurite growth. Neuroscience 2006; 143:501-514.

[20] Jankowski M P, Lawson J J, McIlwrath S L, Rau K K, Anderson C E, Albers K M, Koerber H R. Sensitization of cutaneous nociceptors after nerve transection and regeneration: possible role of target-derived neurotrophic factor signaling. J. Neurosci. 2009; 29:1636-47. doi:10.1523/JNEUROSCI.3474-08.2009.

[21] Jankowski M P, McIlwrath S L, Jing X, Cornuet P K, Salerno K M, Koerber H R, Albers K M. Sox11 transcription factor modulates peripheral nerve regeneration in adult mice. Brain Res. 2009; 1256:43-54. doi:10.1016/j.brainres.2008.12.032.

[22] Jankowski M P, Rau K K, Soneji D J, Anderson C E, Koerber H R. Enhanced artemin/GFRa3 levels regulate mechanically insensitive, heat-sensitive C-fiber recruitment after axotomy and regeneration. J. Neurosci. 2010; 30:16272-16283.

[23] Jankowski M P, Rau K K, Soneji D J, Ekmann K M, Anderson C E, Molliver D C, Koerber H R. Purinergic receptor P2Y1 regulates polymodal C-fiber thermal thresholds and sensory neuron phenotypic switching during peripheral inflammation. Pain 2012; 153:410-419. doi:10.1016/j.pain.2011.10.042.

[24] Jankowski M P, Ross J L, Weber J D, Lee F B, Shank A T, Hudgins RC. Age-dependent sensitization of cutaneous nociceptors during developmental inflammation. Mol Pain 2014; 10:34. doi:10.1186/1744-8069-10-34.

[25] Jennings E, Fitzgerald M. Postnatal changes in responses of rat dorsal horn cells to afferent stimulation: a fibre-induced sensitization. J. Physiol. 1998; 509 (Pt 3:859-68. doi:10.1111/j.1469-7793.1998.859bm.x.

[26] Kastrup, Y, Le Greves, M, Nyberg, F, Blomqvist A. Distribution of growth hormone receptor mRNA in the brain and spinal cord of the rat. Neuroscience 2005; 130:419-25.

[27] Koch S C, Tochiki K K, Hirschberg S, Fitzgerald M. C-fiber activity-dependent maturation of glycinergic inhibition in the spinal dorsal horn of the postnatal rat. Proc. Natl. Acad. Sci. 2012; 109:12201-12206. doi:10.1073/pnas.1118960109.

[28] Koltzenburg M, Stucky C L, Lewin G R. Receptive Properties of Mouse Sensory Neurons Innervating Hairy Skin. J Neurophysiol 1997; 78:1841-1850. Available: http://jn.physiology.org/content/78/4/1841.short. Accessed 22 Oct. 2015.

[29] Kress M, Koltzenburg M, Reeh P W, Handwerker H O. Responsiveness and functional attributes of electrically localized terminals of cutaneous C-fibers in vivo and in vitro. J Neurophysiol 1992; 68:581-595. Available: http://jn.physiology.org/content/68/2/581.short. Accessed 9 Jun. 2016.

[30] Kurimoto K, Yabuta Y, Ohinata Y, Ono Y, Uno K D, Yamada R G, Ueda H R, Saitou M. An improved single-cell cDNA amplification method for efficient high-density oligonucleotide microarray analysis. Nucleic Acids Res. 2006; 34:e42. doi:10.1093/nar/gkl050.

[31] Landis C A, Lentz M J, Rothermel J, Riffle S C, Chapman D, Buchwald D, Shaver J L. Decreased nocturnal levels of prolactin and growth hormone in women with fibromyalgia. J. Clin. Endocrinol. Metab. 2001; 86:1672-8. doi:10.1210/jcem.86.4.7427.

[32] Lanning N J, Carter-Su C. Recent advances in growth hormone signaling. Rev. Endocr. Metab. Disord. 2007; 7:225-235. doi:10.1007/s11154-007-9025-5.

[33] Lawson J J, McIlwrath S L, Woodbury C J, Davis B M, Koerber HR. TRPV1 Unlike TRPV2 Is Restricted to a Subset of Mechanically Insensitive Cutaneous Nociceptors Responding to Heat. J. Pain 2008; 9:298-308. doi:10.1016/j.jpain.2007.12.001.

[34] Leal-Cerro A, Povedano J, Astorga R, Gonzalez M, Silva H, Garcia-Pesquera F, Casanueva F F, Dieguez C. The growth hormone (GH)-releasing hormone-GH-insulin-like growth factor-1 axis in patients with fibromyalgia syndrome. J. Clin. Endocrinol. Metab. 1999; 84:3378-81. doi:10.1210/jcem.84.9.5982.

[35] Lee S-M, Vasishtha M, Prywes R. Activation and repression of cellular immediate early genes by serum response factor cofactors. J. Biol. Chem. 2010; 285:22036-22049.

[36] Li J, Baccei M L. Excitatory synapses in the rat superficial dorsal horn are strengthened following peripheral inflammation during early postnatal development. Pain 2009; 143:56-64. doi:10.1016/j.pain.2009.01.023.

[37] Li J, Baccei M L. Pacemaker neurons within newborn spinal pain circuits. J. Neurosci. 2011; 31:9010-9022.

[38] Li X, Eisenach J C. 2A-Adrenoceptor Stimulation Reduces Capsaicin-Induced Glutamate Release from Spinal Cord Synaptosomes. 2001; 299:939-944.

[39] De Lima J, Alvares D, Hatch D J, Fitzgerald M. Sensory hyperinnervation after neonatal skin wounding: effect of bupivacaine sciatic nerve block. Br. J. Anaesth. 1999; 83:662-664. doi:10.1093/bj a/83.4.662.

[40] Luo W, Enomoto H, Rice F L, Milbrandt J, Ginty D D. Molecular identification of rapidly adapting mechanoreceptors and their developmental dependence on ret signaling. Neuron 2009; 64:841-56. doi:10.1016/j.neuron.2009.11.003.

[41] Luo W, Wickramasinghe S R, Savitt J M, Griffin J W, Dawson T M, Ginty D D. A Hierarchical NGF Signaling Cascade Controls Ret-Dependent and Ret-Independent Events during Development of Nonpeptidergic DRG Neurons. Neuron 2007; 54:739-754. doi:10.1016/j.neuron.2007.04.027.

[42] Malemud C J. The basis for medical therapy of fibromyalgia with growth hormone. Pain 2012; 153:1342-1343.

[43] Malin S A, Davis B M, Molliver D C. Production of dissociated sensory neuron cultures and considerations for their use in studying neuronal function and plasticity. Nat. Protoc. 2007; 2:152-60. doi:10.1038/nprot.2006.461.

[44] Marsh D, Dickenson A, Hatch D, Fitzgerald M. Epidural opioid analgesia in infant rats II: responses to carrageenan and capsaicin. Pain 1999; 82:33-38. doi: 10.1016/S0304-3959(99)00029-9.

[45] Mearow K M, Kril Y, Diamond J. Increased NGF mRNA expression in denervated rat skin. Neuroreport 1993; 4:351-4. Available: http://www.ncbi.nlm.nih.gov/pubmed/8499587. Accessed 23 Oct. 2015.

[46] Miura M, Sasaki M, Mizukoshi K, Shibasaki M, Izumi Y, Shimosato G, Amaya F. Peripheral sensitization caused by insulin-like growth factor 1 contributes to pain hypersensitivity after tissue injury. Pain 2011; 152:888-895.

[47] Molliver D., Wright D., Leitner M., Parsadanian A S, Doster K, Wen D, Yan Q, Snider W. IB4-Binding DRG Neurons Switch from NGF to GDNF Dependence in Early Postnatal Life. Neuron 1997; 19:849-861. doi: 10.1016/S0896-6273(00)80966-6.

[48] Molliver D C, Rau K K, McIlwrath S L, Jankowski M P, Koerber H R. The ADP receptor P2Y1 is necessary for normal thermal sensitivity in cutaneous polymodal nociceptors. Mol. Pain 2011;7:13. doi:10.1186/1744-8069-7-13.

[49] Nathan a., Rose J B, Guite J W, Hehir D, Milovcich K. Primary Erythromelalgia in a Child Responding to Intravenous Lidocaine and Oral Mexiletine Treatment. Pediatrics 2005; 115:e504-e507. doi: 10.1542/peds.2004-1395.

[50] Pogatzki E M, Gebhart G F, Brennan T J. Characterization of Adelta- and C-fibers innervating the plantar rat hindpaw one day after an incision. J. Neurophysiol. 2002; 87:721-731.

[51] Pu S F, Zhuang H X, Marsh D J, Ishii D N. Insulin-like growth factor-II increases and IGF is required for postnatal rat spinal motoneuron survival following sciatic nerve axotomy. J. Neurosci. Res. 1999; 55:9-16. doi: 10.1002/(SICD1097-4547(19990101)55:1<9::AID-JNR2>3.0.CO;2-J.

[52] Reynolds M L, Ward A, Graham C F, Coggeshall R F M. Decreased skin sensory innervation in transgenic mice overexpressing insulin-like growth factor-II. Neuroscience 1997; 79:789-797.

[53] Rhodin a., von EHREN M, Skottheim B, Gronbladh a., Ortiz-Nieto F, Raininko R, Gordh T, Nyberg F. Recombinant human growth hormone improves cognitive capacity in a pain patient exposed to chronic opioids. Acta Anaesthesiol. Scand. 2014; 58:759-765. doi:10.1111/aas.12309.

[54] Ririe D G, Vernon T L, Tobin J R, Eisenach J C. Age-dependent Responses to Thermal Hyperalgesia and Mechanical Allodynia in a Rat Model of Acute Postoperative Pain. Anesthesiology 2003; 99:443-448. doi:10.1097/00000542-200308000-00027.

[55] Ritter a M, Lewin G R, Kremer N E, Mendell L M. Requirement for nerve growth factor in the development of myelinated nociceptors in vivo. Nature 1991; 350:500-502.

[56] Ritter a M, Woodbury C J, Albers K, Davis B M, Koerber H R. Maturation of cutaneous sensory neurons from normal and NGF-overexpressing mice. J. Neurophysiol. 2000; 83:1722-1732. Available: http://www.ncbi.nlm.nih.gov/pubmed/10712492.

[57] Rosenfeld R G, Hwa V. The growth hormone cascade and its role in mammalian growth. Horm. Res. 2009; 71:36-40.

[58] Ross J L, Queme L Q, Cohen ER, Green K J, Lu P, Shank A T, An S, Hudgins R C and J M. Muscle IL1β drives ischemic myalgia via ASIC3-mediated sensory neuron sensitization. J Neurosci. 2016; In press.

[59] Ross J L, Queme L F, Shank A T, Hudgins R C, Jankowski M P. Sensitization of group III and IV muscle afferents in the mouse after ischemia and reperfusion injury. J. Pain 2014; 15:1257-70. doi:10.1016/j.jpain.2014.09.003.

[60] Salomon F, Cuneo R C, Hesp R, Sonksen P H. The Effects of Treatment with Recombinant Human Growth Hormone on Body Composition and Metabolism in Adults with Growth Hormone Deficiency. 2010. Available: http://www.nejm.org/doi/full/10.1056/NEJM198912283212605. Accessed 9 Jun. 2016.

[61] Shim B, Kim D W, Kim B H, Nam T S, Leem J W, Chung J M. Mechanical and heat sensitization of cutaneous nociceptors in rats with experimental peripheral neuropathy. Neuroscience 2005; 132:193-201.

[62] Sonntag W E, Csiszar A, De Cabo R, Ferrucci L, Ungvari Z. Diverse roles of growth hormone and insulin-like growth factor-1 in mammalian aging: Progress and controversies. Journals Gerontol.—Ser. A Biol. Sci. Med. Sci. 2012; 67 A:587-598.

[63] Souza F M, Collett-Solberg P F. Adverse effects of growth hormone replacement therapy in children. Arq. Bras. Endocrinol. Metabol. 2011; 55:559-565. doi:10.1590/S0004-27302011000800009.

[64] Talhouk R S, Saade N E, Mouneimne G, Masaad C a., Safieh-Garabedian B. Growth hormone releasing hormone reverses endotoxin-induced localized inflammatory hyperalgesia without reducing the unregulated cytokines, nerve growth factor and gelatinase activity. Prog. Neuro-Psychopharmacology Biol. Psychiatry 2004; 28:625-631.

[65] Torsney C, Fitzgerald M. Age-dependent effects of peripheral inflammation on the electrophysiological properties of neonatal rat dorsal horn neurons. J. Neurophysiol. 2002; 87:1311-7. Available: http://jn.physiology.org/content/87/3/1311.abstract. Accessed 23 Oct. 2015.

[66] Valdés J a., Flores S, Fuentes E N, Osorio-Fuentealba C, Jaimovich E, Molina A, Choi Y S, Cho H Y, Hoyt K R, Naegele J R, Obrietan K, Zheng W-H, Quirion R. IGF-1 induces IP3-dependent calcium signal involved in the regulation of myostatin gene expression mediated by NFAT during myoblast differentiation. BMC Neurosci. 2013; 56:791-800.

[67] Varco-Merth B, Rotwein P. Differential effects of STAT proteins on growth hormone-mediated IGF-I gene expression. Am. J. Physiol. Endocrinol. Metab. 2014; 307: E847-55. doi:10.1152/ajpendo.00324.2014.

[68] Walker S M, Beggs S, Baccei M L. Persistent changes in peripheral and spinal nociceptive processing after early tissue injury. Exp. Neurol. 2016. doi:10.1016/j.expneurol.2015.06.020.

[69] Walker S M, Meredith-Middleton J, Cooke-Yarborough C, Fitzgerald M. Neonatal inflammation and primary afferent terminal plasticity in the rat dorsal horn. Pain 2003; 105:185-195.

[70] Waters M J, Hoang H N, Fairlie D P, Pelekanos R a., Brown R J. New insights into growth hormone action. J. Mol. Endocrinol. 2006; 36:1-7.

[71] Ye Y, Woodbury C J. Early postnatal loss of heat sensitivity among cutaneous myelinated nociceptors in Swiss-Webster mice. J Neurophysiol 2010; 103:1385-1396. doi:10.1152/jn.00472.2009.

[72] Yu Z-B, Dong X-Y, Han S-P, Chen Y-L, Qiu Y-F, Sha L, Sun Q, Guo X-R. Transcutaneous bilirubin nomogram for predicting neonatal hyperbilirubinemia in healthy term and late-preterm Chinese infants. Eur. J. Pediatr. 2011; 170:185-91. doi:10.1007/s00431-010-1281-9.

[73] Zhang C, Li G, Liang S, Xu C, Zhu G, Wang Y, Zhang A, Wan F. Myocardial ischemic nociceptive signaling mediated by P2X3 receptor in rat stellate ganglion neurons. Brain Res. Bull. 2008; 75:77-82. doi:10.1016/j.brainresbull.2007.07.031.

[74] Zhang Y, Qin W, Qian Z, Liu X, Wang H, Gong S, Sun Y-G, Snutch T P, Jiang X, Tao J. Peripheral pain is enhanced by insulin-like growth factor 1 through a G protein-mediated stimulation of T-type calcium channels. Sci. Signal. 2014; 7:ra94-a94. doi:10.1126/scisignal.2005283.

[75] Zheng W-H, Quirion R. Insulin-like growth factor-1 (IGF-1) induces the activation/phosphorylation of Akt kinase and cAMP response element-binding protein (CREB) by activating different signaling pathways in PC12 cells. BMC Neurosci. 2006; 7:51.

All percentages and ratios are calculated by weight unless otherwise indicated.

All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of treating cutaneous or muscle incision pain in a mammal in need thereof, comprising administering human growth hormone to said mammal.

2. The method of claim 1, wherein said mammal is selected from a human neonate, a human child, a human juvenile, a human young adult, or a human adult.

3. The method of claim 1, wherein said human growth hormone is administered post-operatively.

4. The method of claim 1, wherein said human growth hormone is administered at a dose of from about 0.1 mg/kg to about 2.5 mg/kg, or from about 1 mg/kg to about 1.5 mg/kg.

5. The method of claim 1 wherein said cutaneous or muscle incision pain is associated with a surgery, and wherein said administering comprises administering human GH three days prior to said surgery, two days prior to said surgery, and one day prior to said surgery.

6. The method of claim 1, wherein a dose of human growth hormone is administered systemically, over a period of from 1 to 5 days, or 2 to 3 days, wherein if said dose is administered in a single day, said dose of human growth hormone is from about 0.3 mg/kg to about 6 mg/kg.

7. The method of claim 1, wherein said human growth hormone is administered topically at a dose of from about 0.1 mg/kg to about 3 mg/kg, or from about 1 mg/kg to about 2 mg/kg.

8. The method of claim 1, wherein said human growth hormone is administered to a site of cutaneous and/or muscle incision.

9. The method of claim 1, wherein said administration of human growth hormone is in an amount that avoids a side effect of human growth hormone administration selected from weight gain, transient fevers, hyperglycemia, or combinations thereof.

10. The method of claim 1, wherein said administration of human growth hormone prevents acute to chronic pain transition.

11. The method of claim 1, wherein said mammal does not have a systemic growth hormone deficiency.

* * * * *

SEQUENCE LISTING

<160> NUMBER OF SEQ ID NOS: 15

<210> SEQ ID NO 1
<211> LENGTH: 19
<212> TYPE: RNA
<213> ORGANISM: Artificial Sequence
<220> FEATURE:
<223> OTHER INFORMATION: Targeting sequence used to design siCON duplex

<400> SEQUENCE: 1
uaaggcuaug aagagauac                                              19

<210> SEQ ID NO 2
<211> LENGTH: 19
<212> TYPE: RNA
<213> ORGANISM: Artificial Sequence
<220> FEATURE:
<223> OTHER INFORMATION: Targeting sequence used to design siCON duplex

<400> SEQUENCE: 2
auguauuggc cuguauuag                                              19

<210> SEQ ID NO 3
<211> LENGTH: 19

```
<212> TYPE: RNA
<213> ORGANISM: Artificial Sequence
<220> FEATURE:
<223> OTHER INFORMATION: Targeting sequence used to design siCON duplex

<400> SEQUENCE: 3
augaacguga auugcucaa                                                    19

<210> SEQ ID NO 4
<211> LENGTH: 18
<212> TYPE: RNA
<213> ORGANISM: Artificial Sequence
<220> FEATURE:
<223> OTHER INFORMATION: Targeting sequence used to design siCON duplex

<400> SEQUENCE: 4
ugguuuacug ucgacuaa                                                     18

<210> SEQ ID NO 5
<211> LENGTH: 19
<212> TYPE: RNA
<213> ORGANISM: Artificial Sequence
<220> FEATURE:
<223> OTHER INFORMATION: si RNA Sequence #1

<400> SEQUENCE: 5
ccaucgaggu uacuaauga                                                    19

<210> SEQ ID NO 6
<211> LENGTH: 21
<212> TYPE: DNA
<213> ORGANISM: Artificial Sequence
<220> FEATURE:
<223> OTHER INFORMATION: GAPDH forward primer

<400> SEQUENCE: 6
atgtgtccgt cgtggatctg a                                                 21

<210> SEQ ID NO 7
<211> LENGTH: 22
<212> TYPE: DNA
<213> ORGANISM: Artificial Sequence
<220> FEATURE:
<223> OTHER INFORMATION: GAPDH reverse primer

<400> SEQUENCE: 7
atgcctgctt caccaccttc tt                                                22

<210> SEQ ID NO 8
<211> LENGTH: 20
<212> TYPE: DNA
<213> ORGANISM: Artificial Sequence
<220> FEATURE:
<223> OTHER INFORMATION: LYS forward primer

<400> SEQUENCE: 8
gccatatcgg ctcgcaaatc                                                   20

<210> SEQ ID NO 9
<211> LENGTH: 21
<212> TYPE: DNA
<213> ORGANISM: Artificial Sequence
<220> FEATURE:
<223> OTHER INFORMATION: LYS reverse primer

<400> SEQUENCE: 9
```

```
aacgaatgcc gaaacctcct c                                           21

<210> SEQ ID NO 10
<211> LENGTH: 20
<212> TYPE: DNA
<213> ORGANISM: Artificial Sequence
<220> FEATURE:
<223> OTHER INFORMATION: GH Receptor forward primer

<400> SEQUENCE: 10
gcctctacac cgatgagtaa                                             20

<210> SEQ ID NO 11
<211> LENGTH: 19
<212> TYPE: DNA
<213> ORGANISM: Artificial Sequence
<220> FEATURE:
<223> OTHER INFORMATION: GH Receptor reverse primer

<400> SEQUENCE: 11
ggaaaggact acaccacct                                              19

<210> SEQ ID NO 12
<211> LENGTH: 24
<212> TYPE: DNA
<213> ORGANISM: Artificial Sequence
<220> FEATURE:
<223> OTHER INFORMATION: TNF(alpha)  forward

<400> SEQUENCE: 12
tcggaaagaa atgtcccagg tgga                                        24

<210> SEQ ID NO 13
<211> LENGTH: 24
<212> TYPE: DNA
<213> ORGANISM: Artificial Sequence
<220> FEATURE:
<223> OTHER INFORMATION: TNF(alpha)  reverse primer

<400> SEQUENCE: 13
tggaactggt tctccttaca gcca                                        24

<210> SEQ ID NO 14
<211> LENGTH: 18
<212> TYPE: DNA
<213> ORGANISM: Artificial Sequence
<220> FEATURE:
<223> OTHER INFORMATION: IL6 forward primer

<400> SEQUENCE: 14
actgatgctg gtgacaac                                               18

<210> SEQ ID NO 15
<211> LENGTH: 21
<212> TYPE: DNA
<213> ORGANISM: Artificial Sequence
<220> FEATURE:
<223> OTHER INFORMATION: IL6 reverse primer

<400> SEQUENCE: 15
ccgacttgtg aagtggtata g                                           21
```